United States Patent
Carrillo, Jr. et al.

(10) Patent No.: US 6,520,951 B1
(45) Date of Patent: Feb. 18, 2003

(54) RAPID EXCHANGE CATHETER WITH DETACHABLE HOOD

(75) Inventors: Oscar R. Carrillo, Jr., Attleboro, MA (US); James Yearick, Shrewsbury, MA (US); Robert C. Allman, Wakefield, MA (US); Fernando Alvarez de Toledo, Concord, MA (US); Michael Ciannella, Marlborough, MA (US); Stephen C. Evans, Westford, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/519,649

(22) Filed: Mar. 6, 2000

Related U.S. Application Data

(63) Continuation-in-part of application No. 09/312,340, filed on May 14, 1999, now Pat. No. 6,346,093, which is a continuation-in-part of application No. 09/080,520, filed on May 18, 1998, now Pat. No. 6,096,009, which is a continuation-in-part of application No. 08/926,200, filed on Sep. 9, 1997, now Pat. No. 6,007,522.

(60) Provisional application No. 60/025,235, filed on Sep. 13, 1996.

(51) Int. Cl.[7] .................. A61M 31/00; A61M 5/178; A61B 5/00
(52) U.S. Cl. .................. 604/516; 600/585; 604/164.13
(58) Field of Search ............................ 607/507, 508, 607/510, 514, 516, 523, 533; 604/165.01, 165.02, 165.04, 164.13; 600/585

(56) References Cited

U.S. PATENT DOCUMENTS

| 1,204,053 A | 11/1916 | Moore |
| 2,623,520 A | 12/1952 | Bamford, Jr. et al. ...... 128/221 |

(List continued on next page.)

FOREIGN PATENT DOCUMENTS

| DE | 41 15 007 A1 | 11/1992 |
| EP | 0 328 760 A2 | 8/1989 |
| EP | 0 388 112 A2 | 9/1990 |
| EP | 0 792 657 A2 | 9/1997 |
| EP | 0 801 955 B1 | 10/1997 |
| WO | WO 92/03963 | 3/1992 |
| WO | WO 96/33764 | 10/1996 |
| WO | WO 98/10820 | 3/1998 |
| WO | WO 98/10821 | 3/1998 |
| WO | WO 99/59664 | 11/1999 |
| WO | WO 00/64500 | 11/2000 |
| WO | WO 00/64900 | 11/2000 |

OTHER PUBLICATIONS

Knecht, Gregory L., M.D. et al., "Double–Channel Fistulotome For Endoscopic Drainage of Pancreatic Pseudocyst", *Gastrointestinal Endoscopy*, vol. 37, No. 3, May/Jun. 1991, pp. 356–357.

Siegel, Jerome H., M.D. et al., "Two New Methods For Selective Bile Duct Cannulation and Sphincterotomy", *Gastrointestinal Endoscopy*, vol. 33, No. 6, Dec. 1987, pp. 438–440.

Arndorfer Inc. Information Sheet, dated on or before Mar. 6, 2000, 7 sheets.

*Primary Examiner*—Sharon Kennedy
(74) *Attorney, Agent, or Firm*—Crompton, Seager & Tufte, LLC

(57) ABSTRACT

A single operator exchange biliary catheter having a common distal lumen. The biliary catheter includes an elongate shaft having a proximal portion defining an ancillary lumen and a distal portion defining a common guidewire and ancillary lumen. The common distal lumen reduces the profile of the distal portion of the shaft. The elongate shaft also includes a proximal guidewire port disposed between the proximal end of the shaft and the distal end of the shaft to facilitate single operator use. A seal may be disposed adjacent the proximal guidewire port to thereby seal the port. Preferably, the shaft includes a single lumen distal portion and a bitumen proximal portion. The single lumen distal portion of the shaft may be curved and may include a tapered or spherically shaped distal tip.

27 Claims, 34 Drawing Sheets

U.S. PATENT DOCUMENTS

| | | | | |
|---|---|---|---|---|
| 3,015,869 | A | 1/1962 | Rapata | 24/213 |
| 3,536,281 | A | 10/1970 | Meehan et al. | 248/73 |
| 4,345,606 | A | 8/1982 | Littleford | 128/784 |
| RE31,855 | E | 3/1985 | Osborne | |
| 4,696,668 | A | 9/1987 | Wilcox | 604/28 |
| 4,748,982 | A | 6/1988 | Horzewski et al. | 128/344 |
| 4,762,129 | A | 8/1988 | Bonzel | 128/344 |
| 4,771,777 | A | 9/1988 | Horzewski et al. | 128/344 |
| 4,781,677 | A | 11/1988 | Wilcox | 604/28 |
| 4,835,824 | A | 6/1989 | Durham et al. | 24/339 |
| 4,844,092 | A | 7/1989 | Rydell et al. | 128/772 |
| 4,900,184 | A | 2/1990 | Cleveland | 403/397 |
| 4,905,667 | A | 3/1990 | Foerster et al. | 128/4 |
| 4,917,103 | A | 4/1990 | Gambale et al. | 128/772 |
| 4,927,418 | A | 5/1990 | Dake et al. | 604/264 |
| 4,928,693 | A | 5/1990 | Goodin et al. | 128/637 |
| 4,932,413 | A | 6/1990 | Shockey et al. | 128/657 |
| 4,946,443 | A | 8/1990 | Hauser et al. | 604/165 |
| 4,973,329 | A | 11/1990 | Park et al. | |
| 4,983,168 | A | 1/1991 | Moorehead | 604/161 |
| 4,988,356 | A | 1/1991 | Crittenden et al. | 606/192 |
| 4,997,421 | A | 3/1991 | Palsrok et al. | 604/174 |
| 5,040,548 | A | 8/1991 | Yock | 128/898 |
| 5,061,273 | A | 10/1991 | Yock | 606/194 |
| 5,064,414 | A | 11/1991 | Revane | 604/165 |
| 5,125,915 | A | 6/1992 | Berry et al. | 604/283 |
| 5,135,535 | A | 8/1992 | Kramer | 606/194 |
| 5,139,032 | A | 8/1992 | Jahrmarkt et al. | |
| 5,147,377 | A | 9/1992 | Sahota | 606/194 |
| 5,158,545 | A | 10/1992 | Trudell et al. | 604/53 |
| 5,167,634 | A | 12/1992 | Corrigan, Jr. et al. | 604/160 |
| 5,191,888 | A | 3/1993 | Palmer et al. | |
| 5,195,978 | A | 3/1993 | Schiffer | 604/161 |
| 5,205,822 | A | 4/1993 | Johnson et al. | 604/96 |
| 5,232,445 | A | 8/1993 | Bonzel | 604/96 |
| 5,248,306 | A | 9/1993 | Clark et al. | 604/283 |
| 5,250,033 | A | 10/1993 | Evans et al. | 604/160 |
| 5,279,562 | A | 1/1994 | Sirhan et al. | 604/96 |
| 5,282,479 | A | 2/1994 | Havran | 128/772 |
| 5,290,232 | A | 3/1994 | Johnson et al. | 604/96 |
| 5,290,241 | A | 3/1994 | Kraus et al. | 604/161 |
| 5,300,085 | A | 4/1994 | Yock | 606/191 |
| 5,306,247 | A | 4/1994 | Pfenninger | 604/96 |
| 5,308,318 | A | 5/1994 | Plassche, Jr. | 604/54 |
| 5,320,602 | A | 6/1994 | Karpiel | 604/54 |
| 5,324,259 | A | 6/1994 | Taylor et al. | 604/96 |
| 5,324,269 | A | 6/1994 | Miraki | 604/160 |
| 5,334,143 | A | 8/1994 | Carroll | 604/54 |
| 5,334,187 | A | 8/1994 | Fischell et al. | 604/194 |
| 5,350,395 | A | 9/1994 | Yock | 606/194 |
| 5,364,355 | A | 11/1994 | Alden et al. | 604/96 |
| 5,364,376 | A | 11/1994 | Horzewski et al. | 604/280 |
| 5,370,623 | A | 12/1994 | Kreamer | 604/165 |
| 5,389,087 | A | 2/1995 | Miraki | 604/247 |
| 5,397,302 | A | 3/1995 | Weaver et al. | 604/54 |
| 5,448,993 | A | 9/1995 | Lynch et al. | |
| 5,451,233 | A | 9/1995 | Yock | 606/194 |
| 5,454,790 | A | 10/1995 | Dubrul | 604/104 |
| 5,458,584 | A | 10/1995 | Ginn et al. | 604/280 |
| 5,458,605 | A | 10/1995 | Klemm | 606/108 |
| 5,480,389 | A | 1/1996 | McWha et al. | 604/165 |
| 5,489,271 | A | 2/1996 | Andersen | 604/102 |
| 5,490,837 | A | 2/1996 | Blaeser et al. | 604/96 |
| 5,496,346 | A | 3/1996 | Horzewski et al. | 606/154 |
| 5,501,227 | A | 3/1996 | Yock | 128/662.06 |
| 5,531,700 | A | 7/1996 | Moore et al. | 604/164 |
| 5,536,248 | A | 7/1996 | Weaver et al. | 604/54 |
| 5,540,236 | A | 7/1996 | Ginn | 128/772 |
| 5,599,299 | A | 2/1997 | Weaver et al. | 604/54 |
| 5,599,300 | A | 2/1997 | Weaver et al. | 604/54 |
| 5,626,600 | A | 5/1997 | Horzewski et al. | 606/194 |
| 5,693,015 | A * | 12/1997 | Walker et al. | 604/96.01 |
| 5,706,827 | A | 1/1998 | Ehr et al. | 128/772 |
| 5,718,680 | A | 2/1998 | Kraus et al. | 604/53 |
| 5,725,504 | A | 3/1998 | Collins | 604/165 |
| 5,788,681 | A | 8/1998 | Weaver et al. | 604/280 |
| 5,800,414 | A | 9/1998 | Cazal | 604/280 |
| 5,833,706 | A | 11/1998 | St. Germain et al. | 606/194 |
| 5,843,028 | A | 12/1998 | Weaver et al. | 604/54 |
| 5,849,016 | A | 12/1998 | Suhr | 606/108 |
| 5,921,971 | A | 7/1999 | Agro et al. | 604/280 |
| 5,935,114 | A | 8/1999 | Jang et al. | |
| 5,978,699 | A | 11/1999 | Fehse et al. | |
| 6,007,522 | A | 12/1999 | Agro et al. | 604/264 |
| 6,096,009 | A | 8/2000 | Windheuser et al. | 604/165 |
| 6,152,910 | A | 11/2000 | Agro et al. | 604/523 |
| 6,277,100 | B1 | 8/2001 | Raulerson et al. | |
| 6,346,093 | B1 | 2/2002 | Allman et al. | |

* cited by examiner

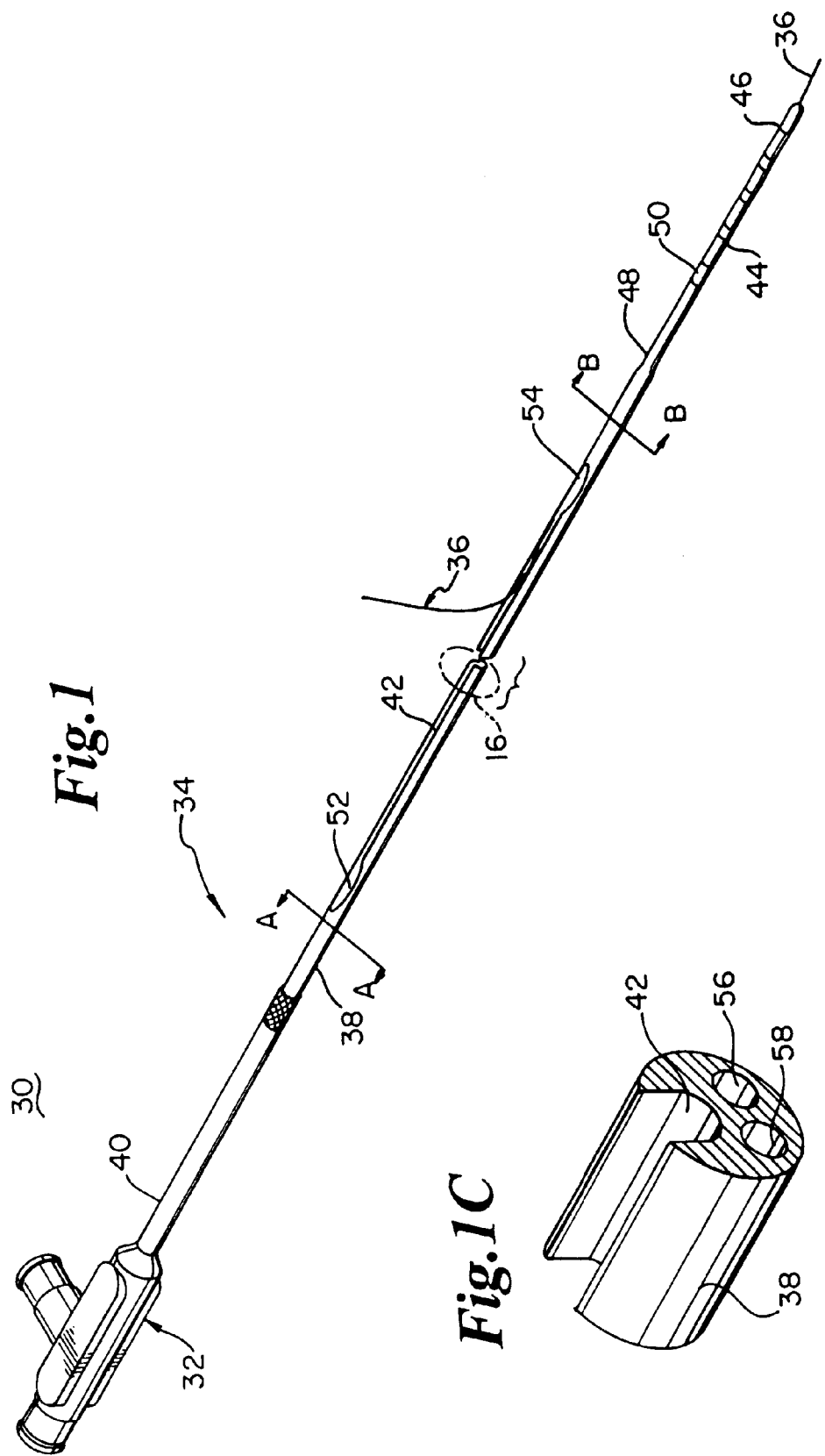

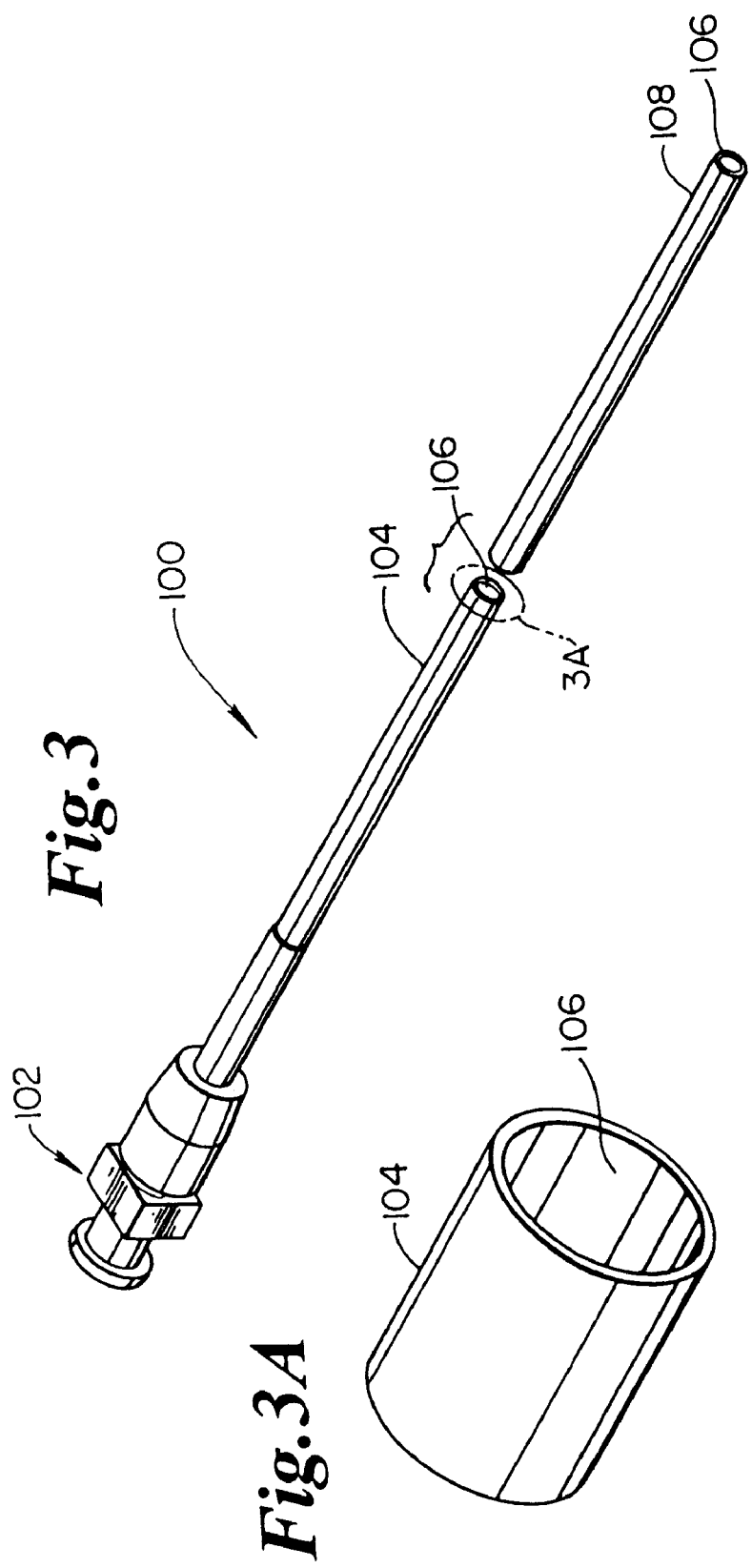

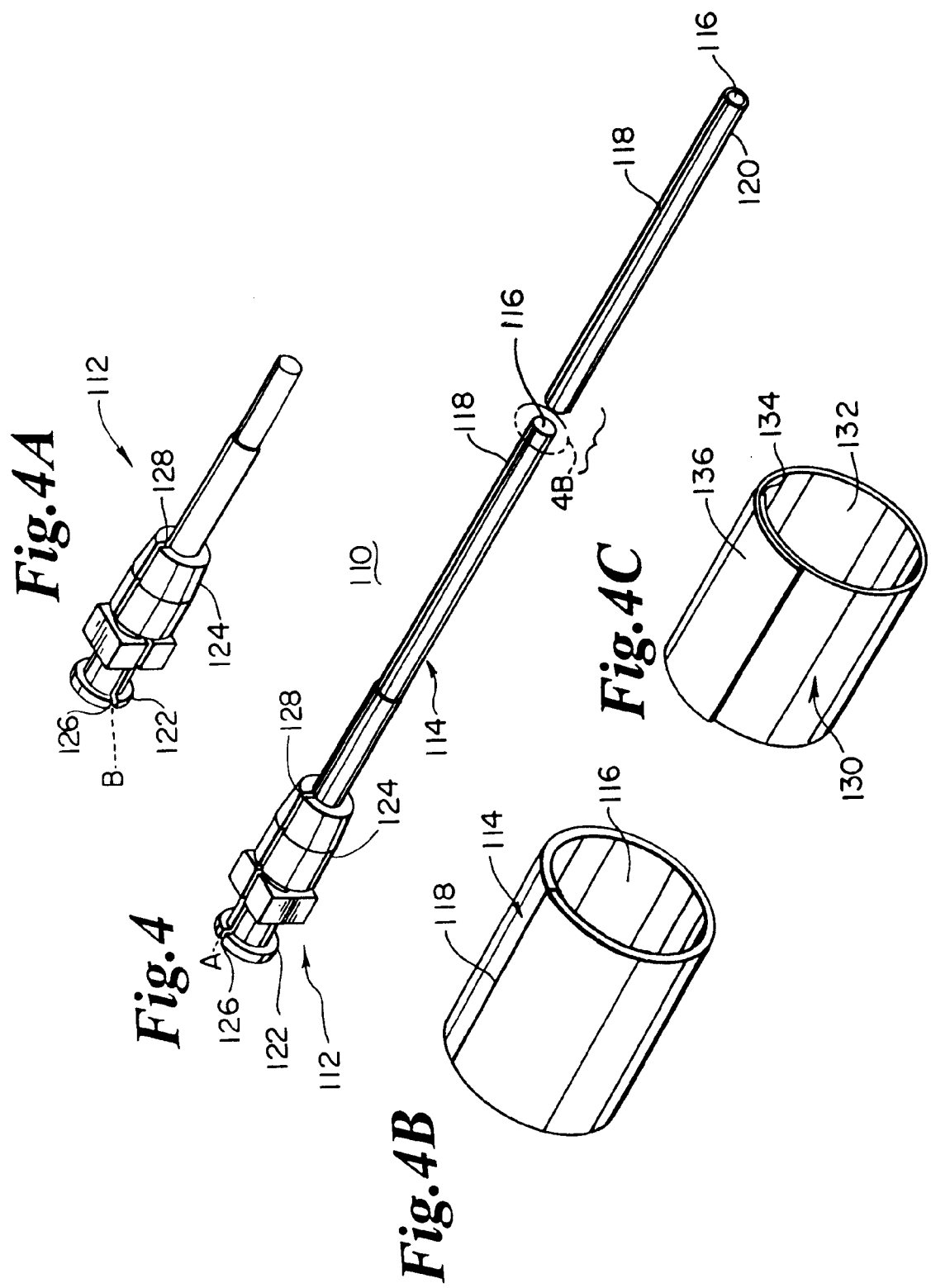

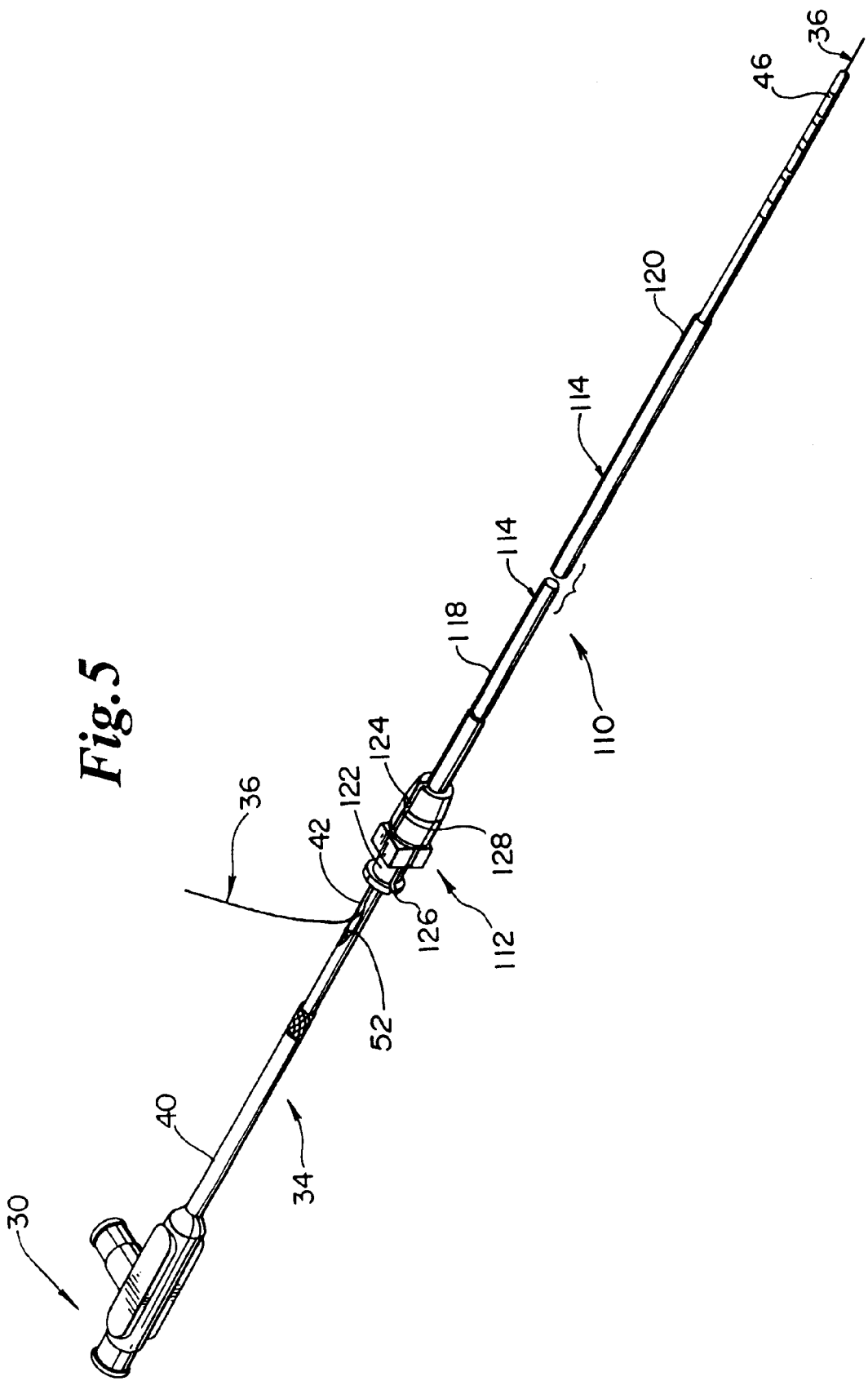

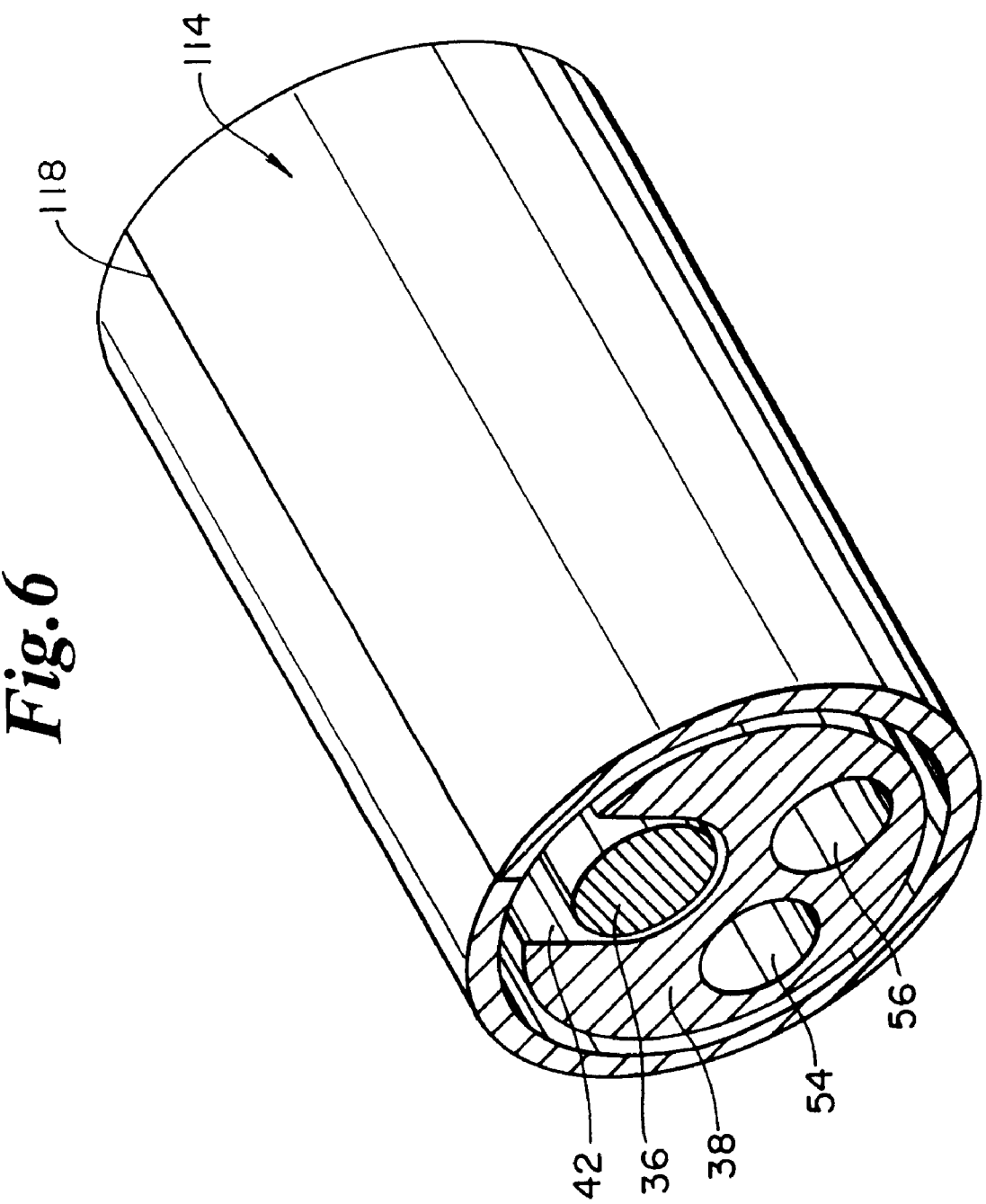

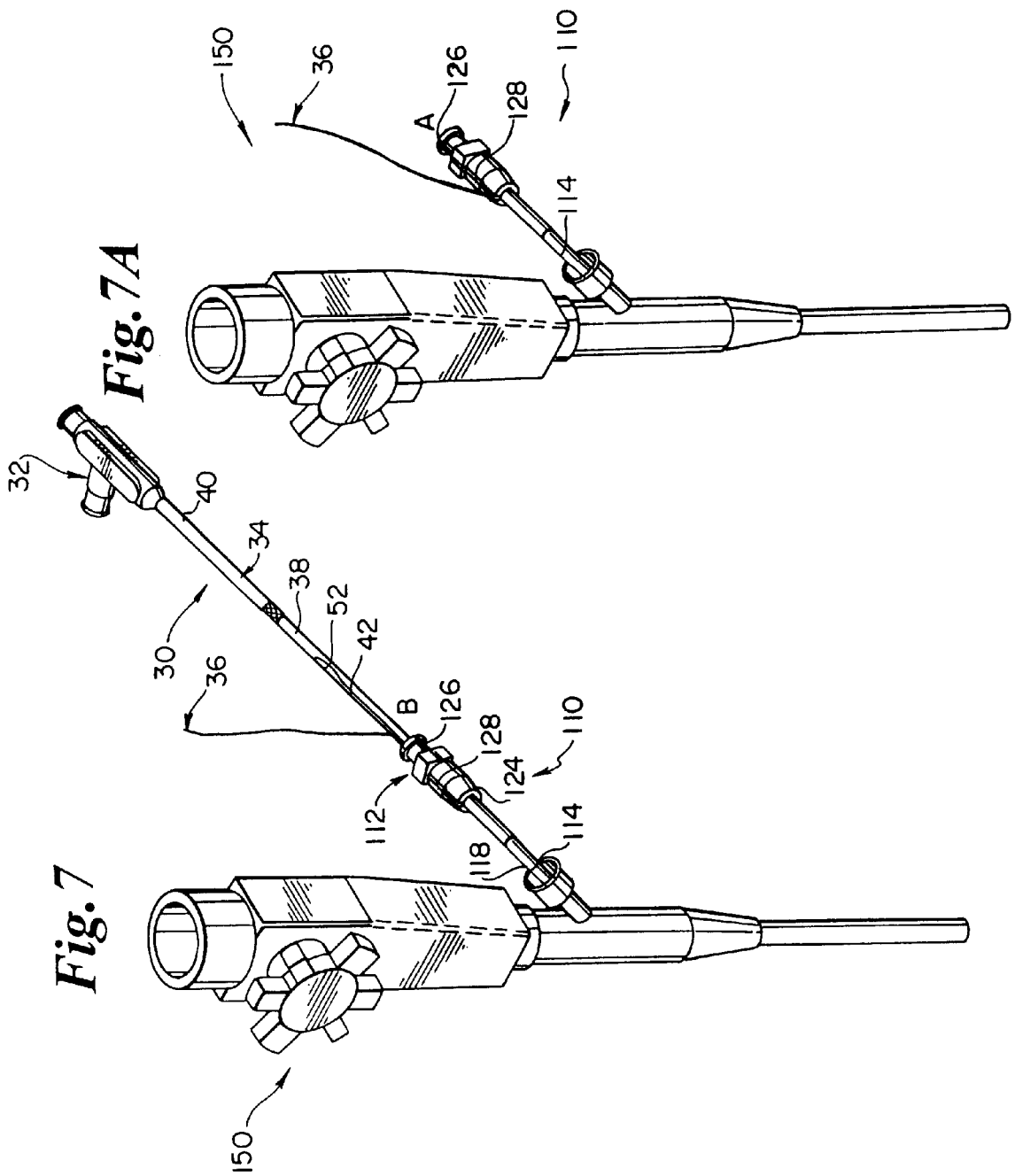

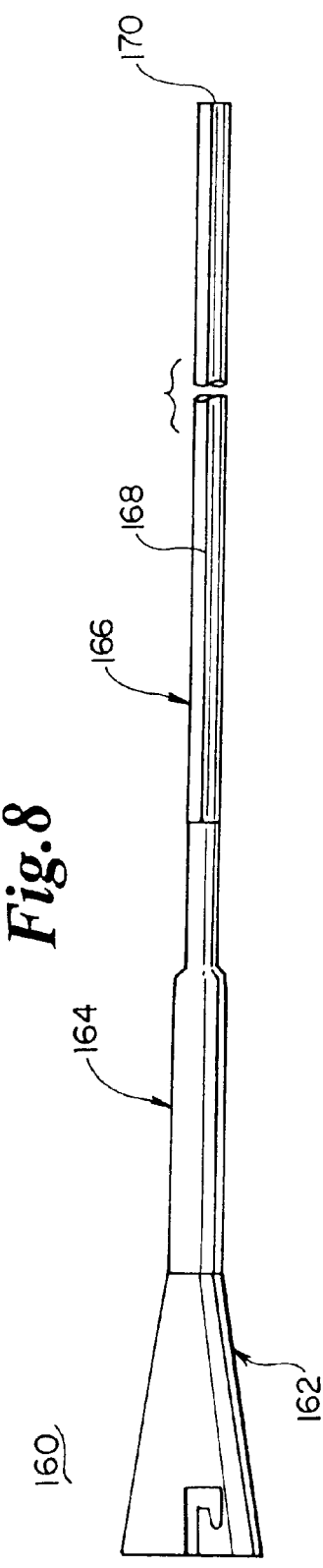
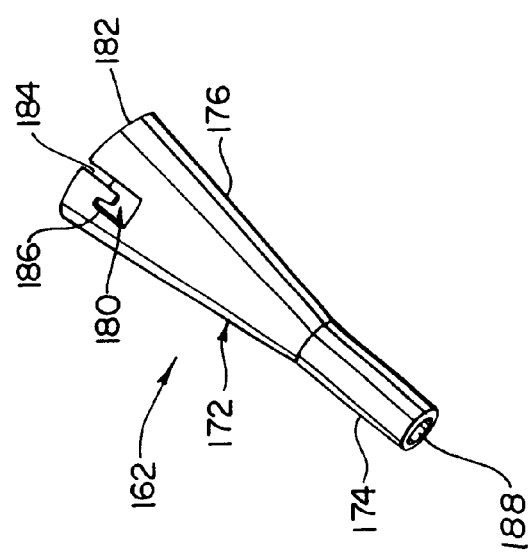

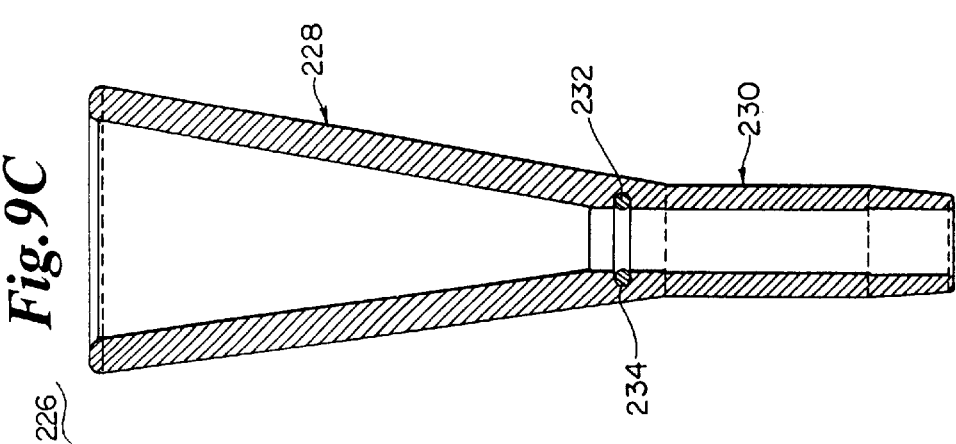
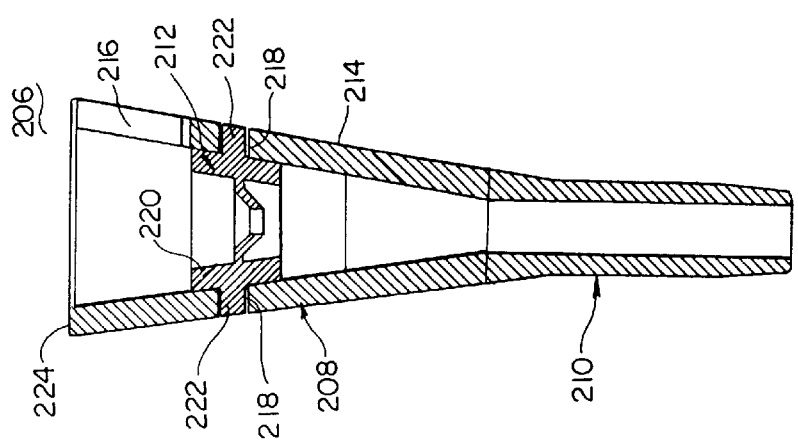
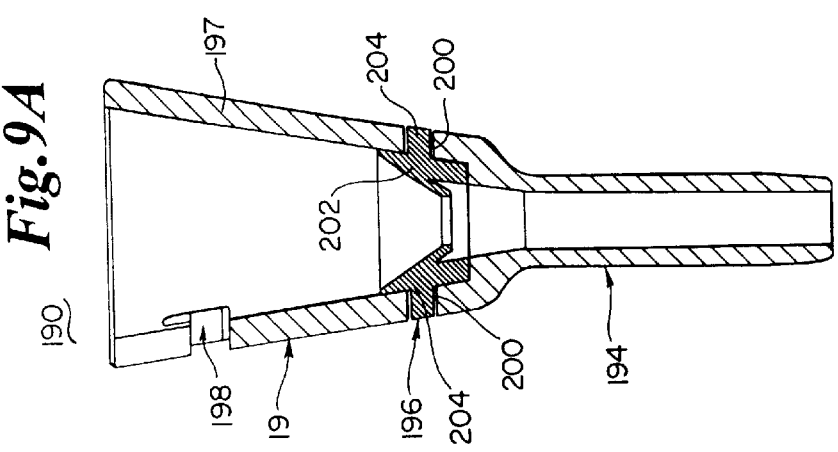

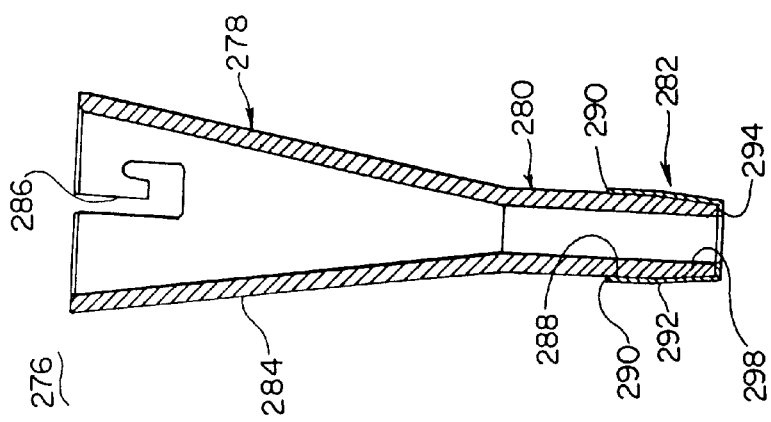
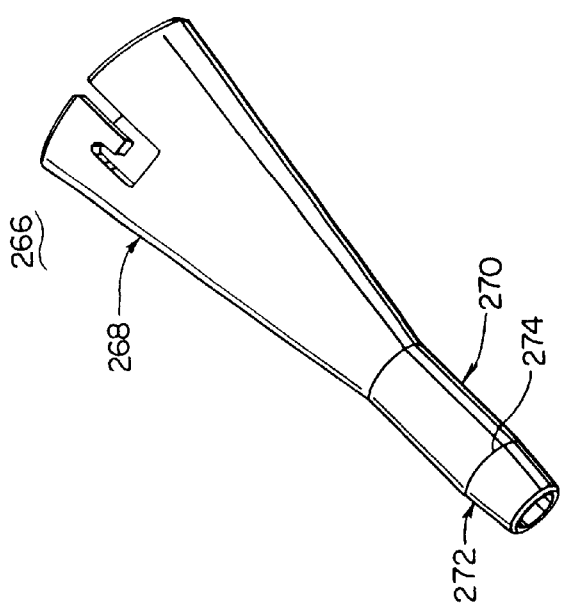
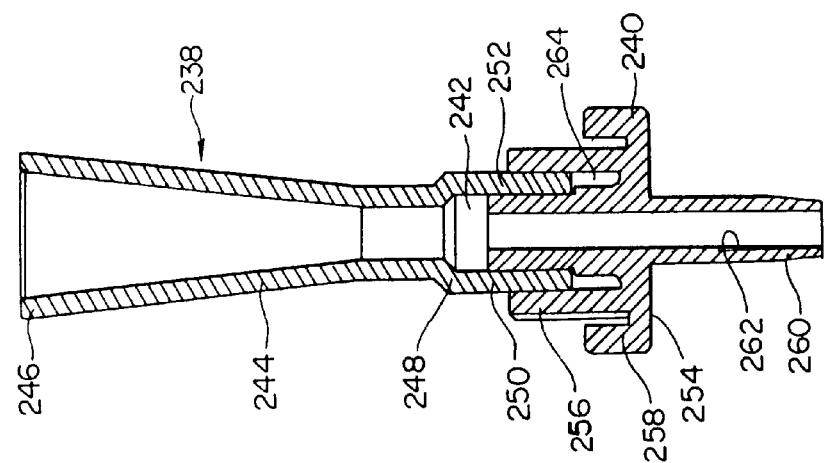

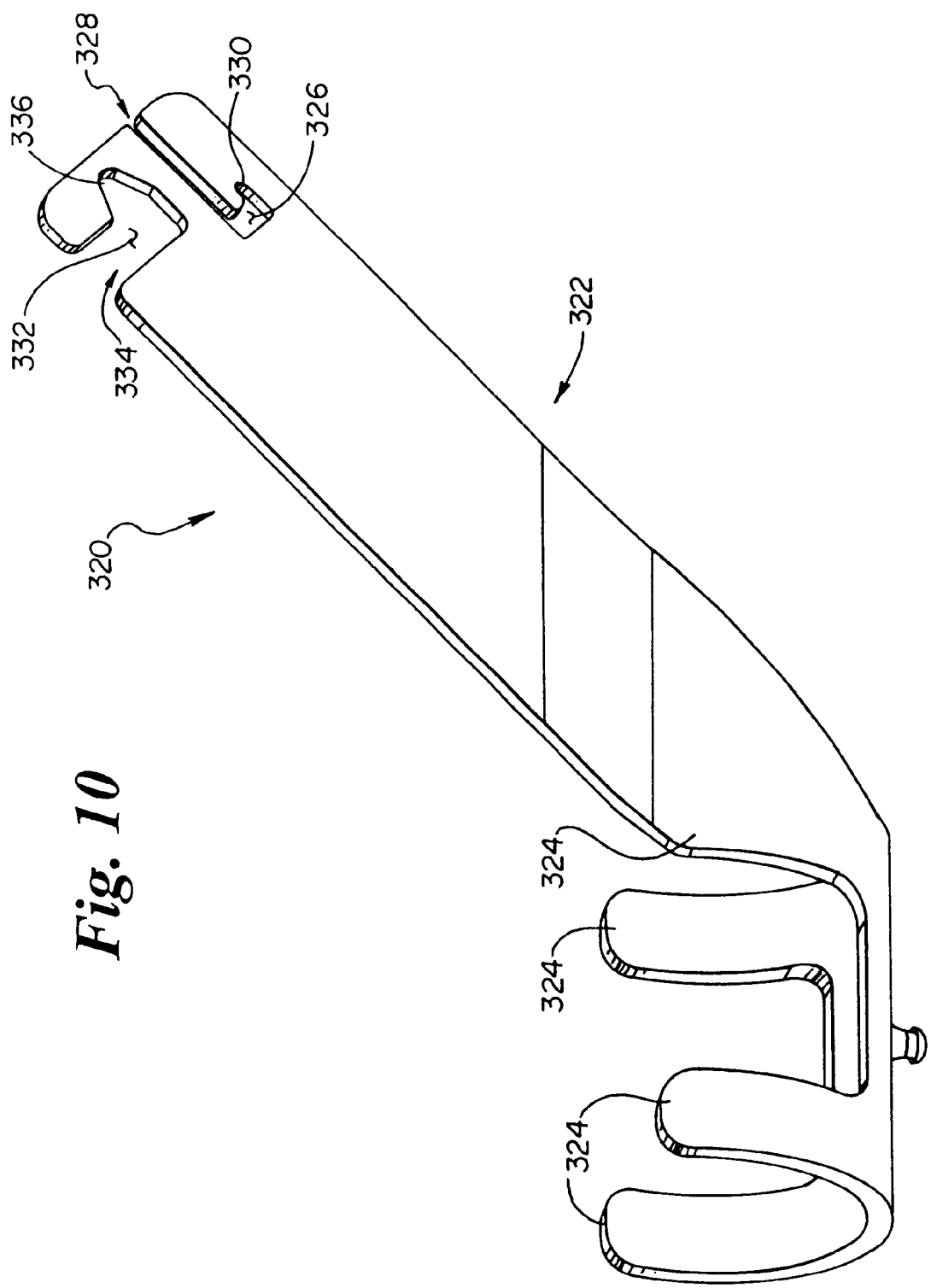

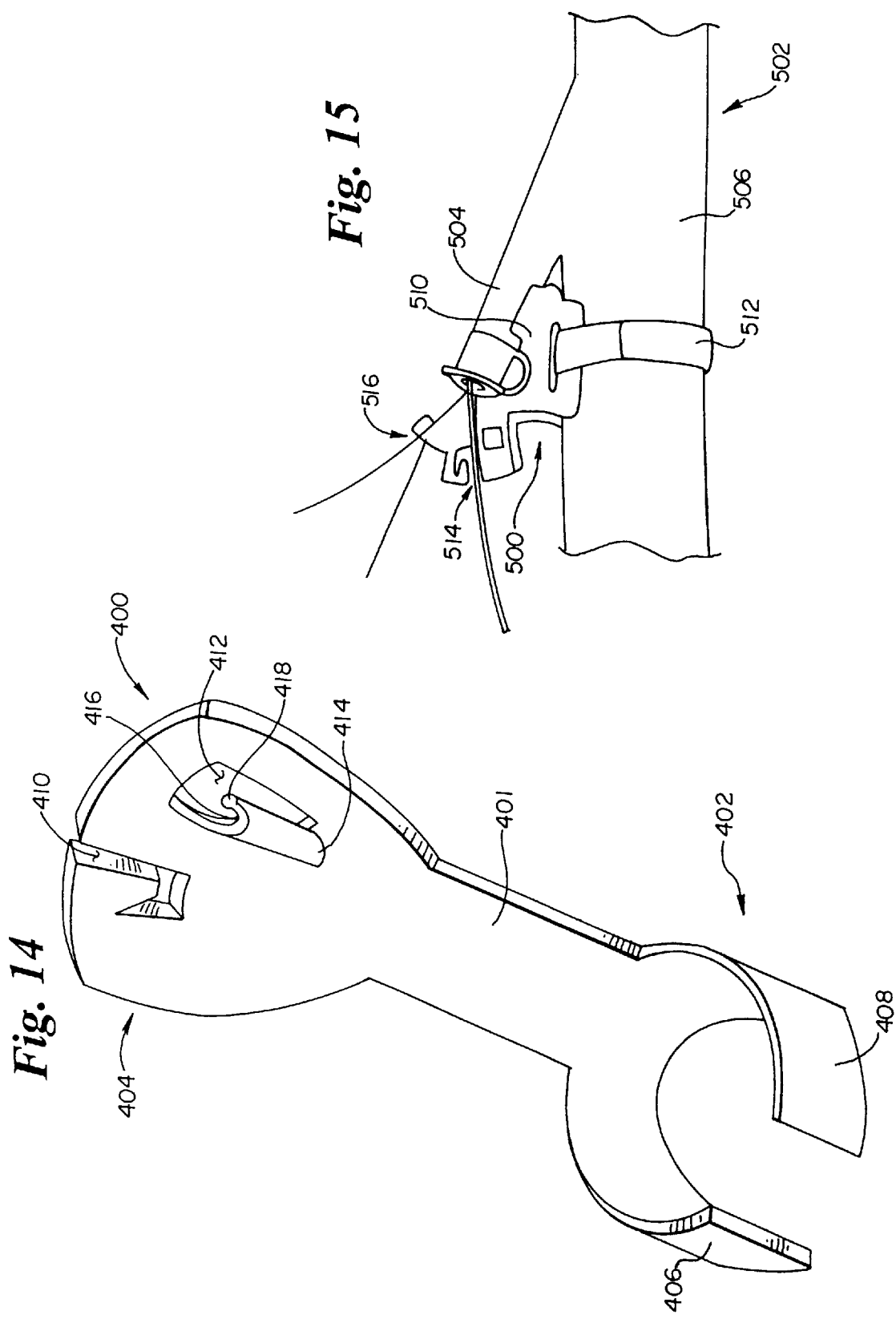

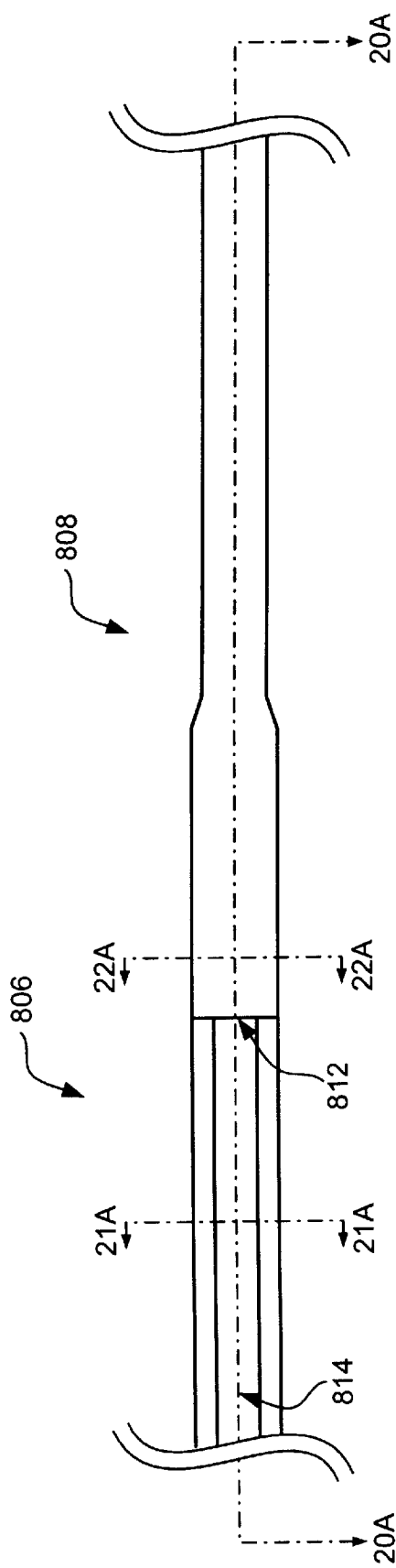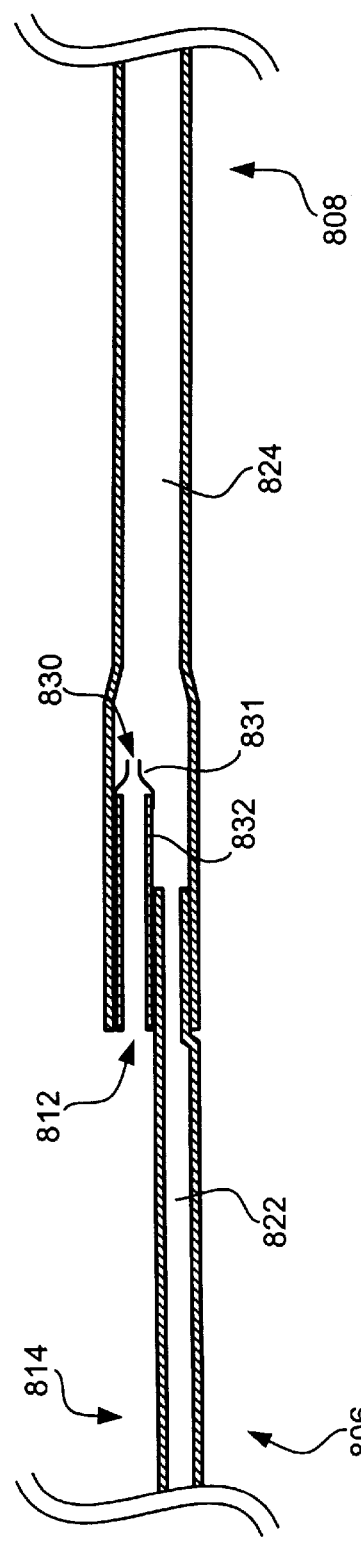
FIG. 19A
FIG. 20A

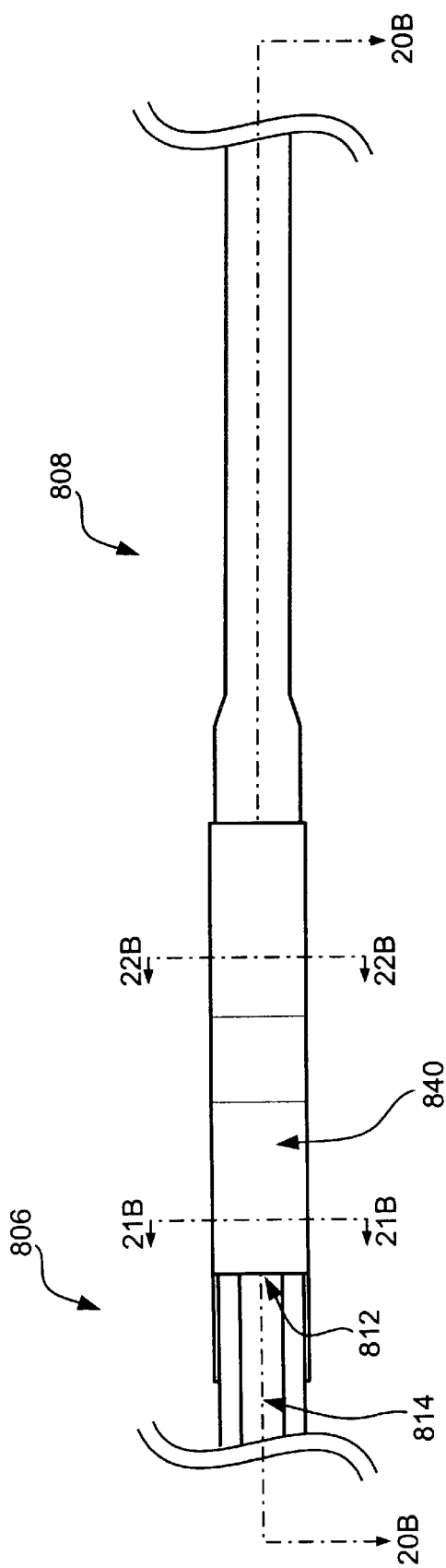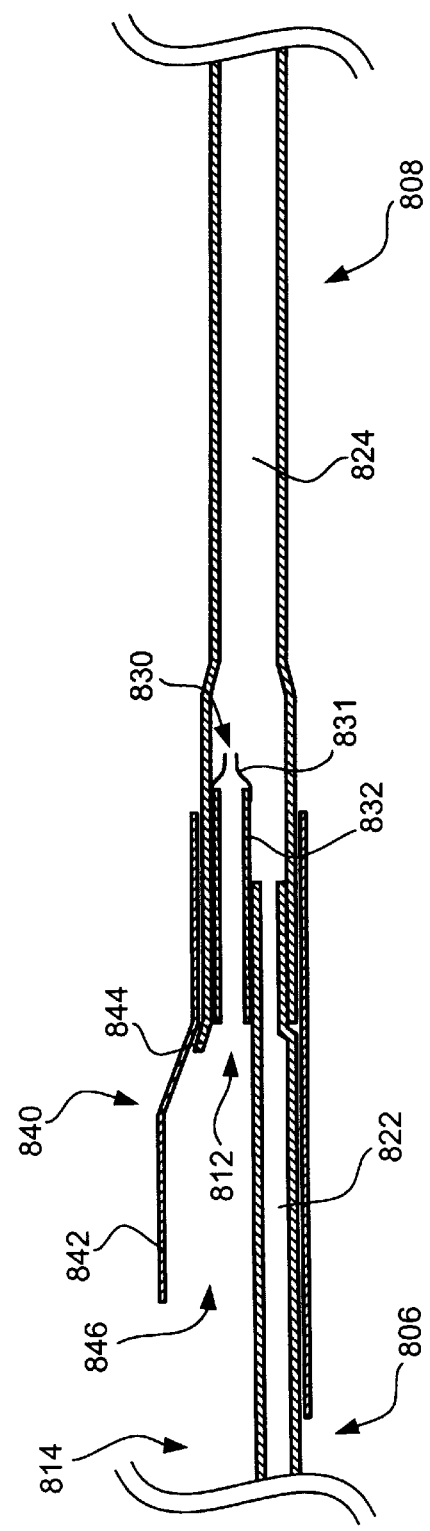

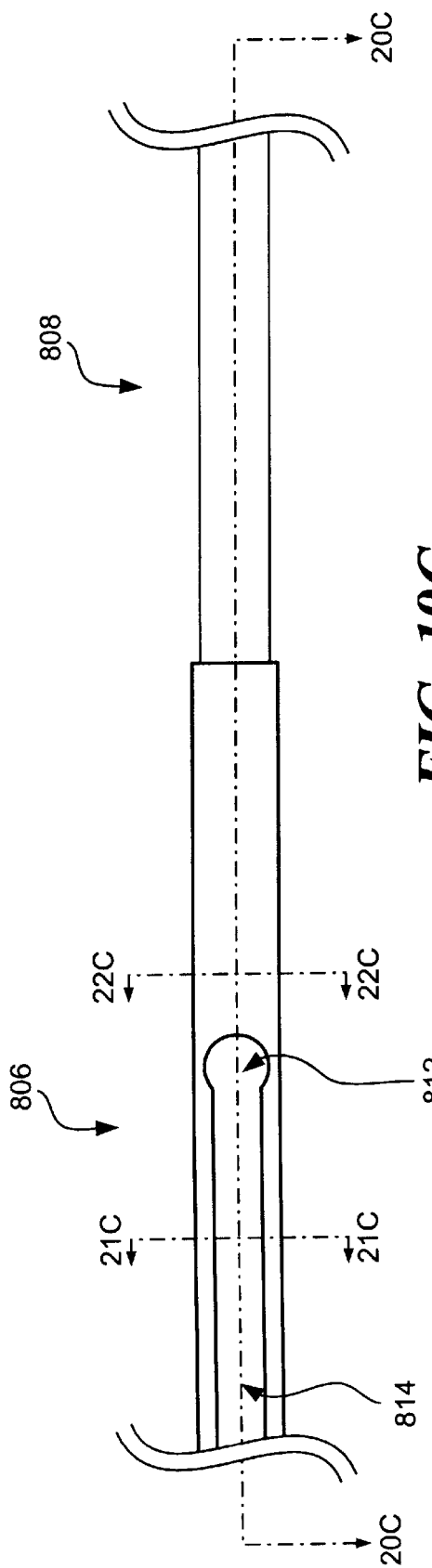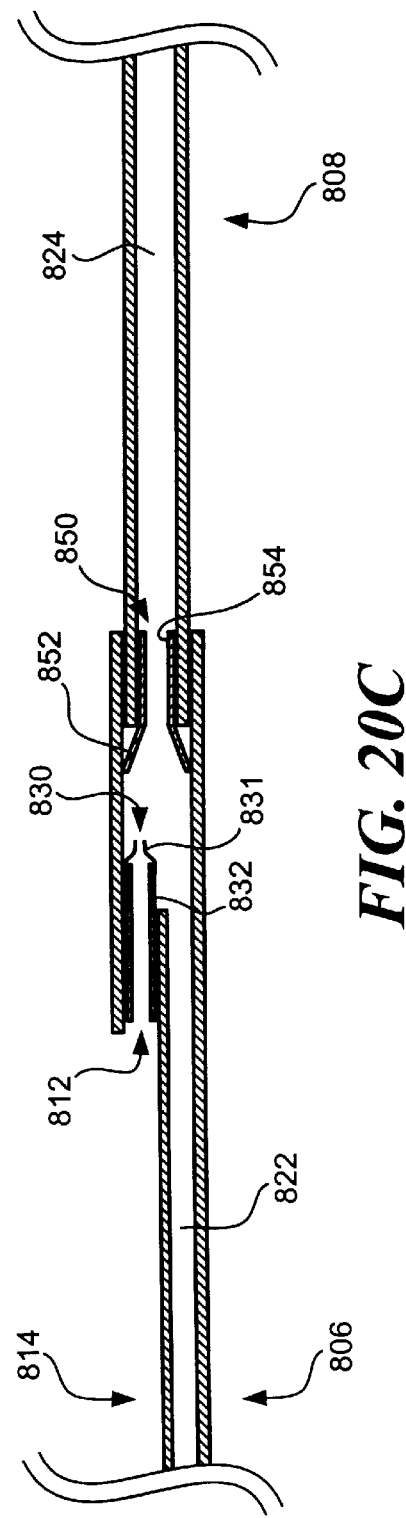

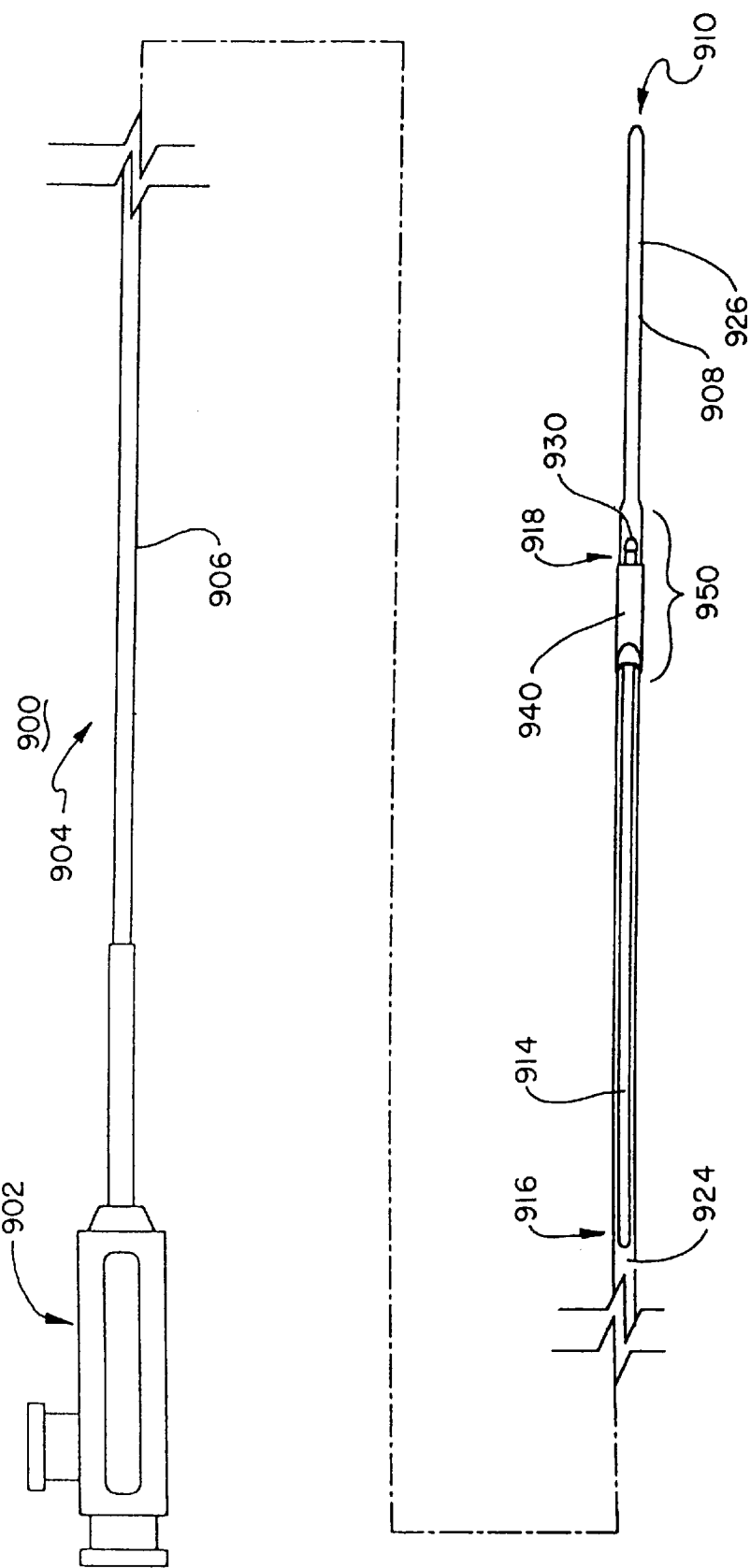

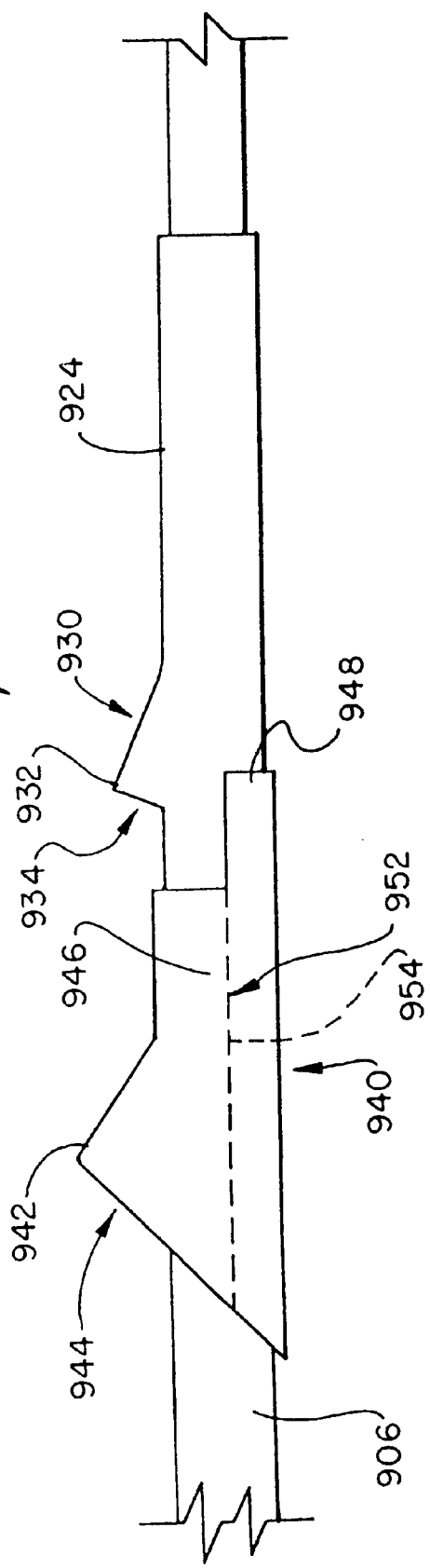

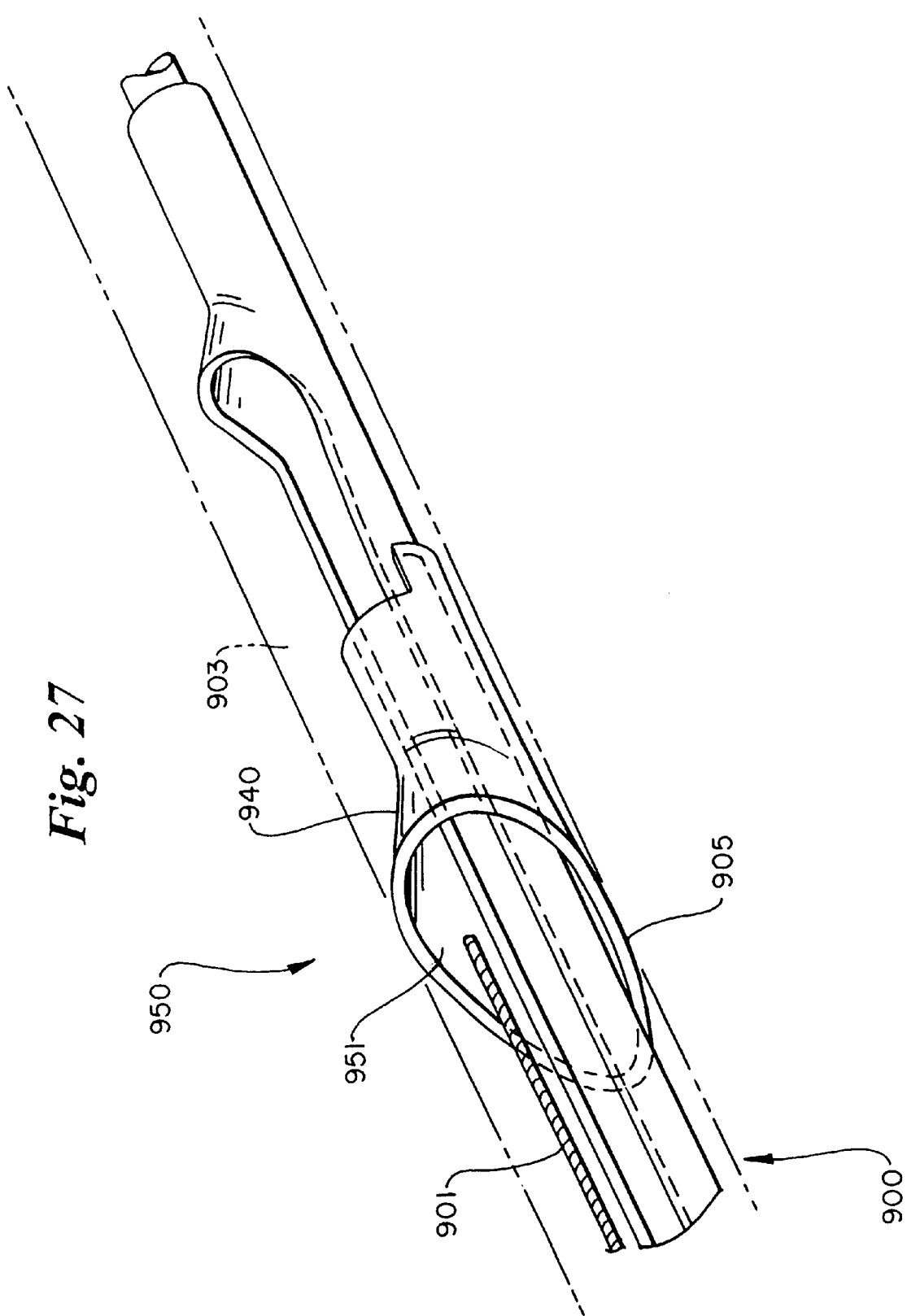

RAPID EXCHANGE CATHETER WITH DETACHABLE HOOD

CROSS REFERENCE TO RELATED APPLICATIONS

This application is a continuation-in-part of U.S. patent Ser. No. 09/312,340 filed on May 14, 1999 U.S. Pat. No. 6,346,093, issued Feb. 12, 2002, entitled "Single Operator Exchange Biliary Catheter with Common Distal Lumen"; which is a continuation-in-part application of U.S. patent Ser. No. 09/080,520 filed on May 18, 1998 now U.S. Pat. No. 6,096,009, issued Aug. 1, 2000, entitled "Guidewire and Catheter Locking Device and Method"; which is a continuation-in-part application of U.S. patent Ser. No. 08/926,200 filed on Sep. 9, 1997 now U.S. Pat. No. 6,007,522, issued Dec. 28, 1999, entitled "Single Operator Exchange Biliary Catheter"; which claims priority to U.S. Provisional Application No. 60/025,235, filed Sep. 13, 1996, entitled "Single Operator Exchange Biliary Catheter", the entire disclosures of which are hereby incorporated by reference. This application is related to U.S. patent application Ser. No. 09/312,438, filed on May 14, 1999, entitled "Guidewire Insertion and Re-insertion Tools and Methods of Use", the entire disclosure of which is hereby incorporated by reference.

FIELD OF THE INVENTION

The present invention generally relates to endoscopic devices and methods of use. Specifically, the present invention relates to catheters for use in combination with guidewires and endoscopes.

BACKGROUND OF THE INVENTION

Endoscopic procedures for treating abnormal pathologies within the alimentary canal system and biliary tree. (including the biliary, hepatic, and pancreatic ducts) are increasing in number. The endoscope provides access to the general area of a desired duct using direct visualization. However, the duct itself must be navigated using a catheter in conjunction with fluoroscopy and guidewires.

Catheters are known for treatment of targeted anatomical regions. Known methods and devices for using biliary catheters for accessing the biliary tree for performing catheter procedures are disclosed in Weaver et al., U.S. Pat. No. 5,397,302 and Karpiel, U.S. Pat. No. 5,320,602, the disclosures of which are herein incorporated by reference. In general, for treatment of an abnormal pathology within a patient's biliary tree, an endoscope is first introduced into the mouth of the patient. The endoscope includes a proximal end and a distal end, and has a lumen extending longitudinally between the proximal and distal ends. The endoscope is guided through the patient's alimentary tract or canal until an opening at the distal end of the endoscope is proximate the area to receive treatment. At this point, the endoscope allows other components, such as a catheter, to access the targeted area.

For visualization or treatment within the biliary tree, the distal end of the endoscope is positioned proximate the papilla of vater leading to the common bile duct and the pancreatic duct. A catheter is guided through the lumen of the endoscope until a distal tip of the catheter emerges from the opening at the distal end of the endoscope.

The catheter may be used for accessing the biliary tree. The distal end of the catheter is guided through the orifice to the papilla of vater (located between the sphincter of oddi) leading to the common bile duct and the pancreatic duct. A guidewire may be used in conjunction with the catheter to facilitate accessing a desired location within the biliary tree. The guidewire is inserted in an opening at a proximal end of the catheter and guided through the catheter until it emerges from the distal end of the catheter.

If visualization of the common bile duct is desired, the guidewire is guided into the common bile duct. The catheter is advanced over the guidewire, as previously described, until the distal end of the catheter is positioned in the common bile duct at the desired location. The catheter is now in position for delivery of contrast media for fluoroscopic visualization of anatomical detail within the common bile duct. Once the guidewire is in place relative to the targeted area, it is highly desirable to maintain that position of the guidewire during subsequent catheter procedures, including catheter exchange procedures.

Present biliary endoscopic procedures include the use of multi-lumen catheters for endoscopic retrograde cholangiopancreatography, endoscopic retrograde sphincterotomy, the use of balloon catheters having retrieval balloons, stenting, and other therapeutic and diagnostic procedures. As described in general above, these present biliary endoscopic procedures are performed using guidewire techniques. The present devices utilized in these procedures are at least 200 cm long since they pass through the endoscope, which is commonly at least 150 cm long. Therefore, when using a standard catheter having a guidewire lumen extending the full length of the catheter, guidewires used during these procedures must be at least 450 cm in length to accommodate the exchanging of different devices while maintaining access and position within the biliary tree. The exchange of devices over a 450 cm guidewire is both time consuming and cumbersome.

Due to the length of the guidewire, physicians require at least two assistants in the room to perform the biliary endoscopic procedure. Typically, one assistant is responsible for the patient and device-related concerns, while the other assistant is responsible for the guidewire. The additional hands required due to the length of the guidewire results in a relatively more time consuming and costly procedure.

It is desirable to have an exchange catheter suitable for use within the alimentary canal for accessing targeted anatomical regions, such as the biliary tree, having features which facilitate rapid exchange and allow an exchange procedure to be performed by a single operator. It is desirable to have a biliary exchange catheter which may be used in connection with a shorter guidewire, and requires less personnel for performing biliary procedures. It is desirable to have a biliary exchange catheter which limits the amount of guidewire over which the catheter must travel.

It is also desirable to have a biliary rapid exchange catheter which may be convertible for use between conventional guidewire techniques and rapid exchange guidewire techniques. It is desirable to have a biliary rapid exchange catheter which is easily removable from the guidewire, and adaptable for use with most catheter systems used within the alimentary canal. It would also be desirable to have an exchange catheter with a low profile distal portion available in a number of different sizes and shapes to accommodate variations in anatomy and provide access to treatment sites that would otherwise be difficult to reach.

SUMMARY OF THE INVENTION

The present invention provides a single operator exchange biliary catheter having a common distal lumen thereby reducing the profile of the distal portion of the shaft. In an exemplary embodiment, the present invention provides a biliary catheter including an elongate shaft having a proximal portion defining an ancillary lumen and a distal portion defining a common guidewire and ancillary lumen. The elongate shaft includes a proximal guidewire port disposed between the proximal end of the shaft and the distal guidewire port to facilitate single operator use.

A seal may be disposed adjacent proximate the guidewire port to thereby seal the port. Preferably, the seal provides a fluid seal with or without the guidewire disposed therein. The seal may be a wide variety of different types, including, but not limited to, a one-way valve type seal.

Preferably, the shaft includes a single lumen distal portion and a bi-lumen proximal portion. The single lumen distal portion of the shaft may include a tapered or spherically shaped distal tip. The bitumen proximal portion may include a longitudinal channel providing access to the proximal guidewire lumen.

In preferred embodiments, a hood may be disposed between the proximal bi-lumen portion and the distal single lumen portion to assist the guidewire in entering the guidewire lumen. Also, a constraint tube may be disposed adjacent the proximal guidewire port to assist the guidewire into the proximal guidewire port.

BRIEF DESCRIPTION OF THE DRAWINGS

FIG. 1 is a perspective view of a single operator exchange catheter in accordance with the present invention;

FIG. 1C is an enlarged fragmentary perspective view of the catheter of FIG. 1 at circle C;

FIG. 3 is a perspective view of an endoscope exchange sheath assembly, without a slit, suitable for receiving the catheter of FIG. 1;

FIG. 3A is an enlarged fragmentary perspective view of the encircled sheath section of FIG. 3 at 3A;

FIG. 4 is a perspective view of an alternative embodiment sheath assembly having a slit sheath and two-piece hub, shown in an unlocked position;

FIG. 4A is a perspective view of the two-piece hub of FIG. 4 in a locked position;

FIG. 4B is an enlarged fragmentary perspective view of the encircled sheath section of FIG. 4 at 4B, having a slit;

FIG. 4C is an enlarged fragmentary perspective view of a sheath section, having an overlap, an alternate embodiment of the sheath in FIG. 4B;

FIG. 5 is a perspective view of the catheter of FIG. 1 inserted through the endoscope sheath assembly of FIG. 4;

FIG. 6 is a perspective view of an endoscope sheath section containing a catheter having a U-shaped channel containing a guidewire;

FIG. 7 is a partial perspective view of a guidewire within the catheter of FIG. 1 inserted through the endoscope sheath assembly of FIG. 4, which is in turn within an endoscope;

FIG. 7A is a perspective view of the sheath assembly of FIG. 7, having the catheter removed;

FIG. 8 is a partial perspective view of an alternative embodiment of a sheath assembly, including an introducer;

FIG. 8A is an enlarged perspective view of the introducer of FIG. 8;

FIG. 9A is an enlarged, cross-sectional view of an alternative embodiment of the introducer of FIG. 8;

FIG. 9B is an enlarged, cross-sectional view of another alternative embodiment of the introducer of FIG. 8;

FIG. 9C is an enlarged, cross-sectional view of another alternative embodiment of the introducer of FIG. 8;

FIG. 9D is an enlarged, cross-sectional view of another alternative embodiment of the introducer of FIG. 8;

FIG. 9E is an enlarged, perspective view of another alternative embodiment of the introducer of FIG. 8;

FIG. 9F is an enlarged, cross-sectional view of another alternative embodiment of the introducer of FIG. 8;

FIG. 10 is a perspective view of an illustrative locking device;

FIG. 14 is a perspective view of yet another illustrative locking device;

FIG. 15 is a partial side view of another illustrative locking device positioned on an endoscope having an angled side port;

FIG. 19A is a detailed side view of a first embodiment of section 19 in FIG. 16;

FIGS. 20A–22A are cross-sectional views taken along lines 20A—20A, 21A—21A and 22A—22A, respectively, in FIG. 19A;

FIG. 19B is a detailed side view of a second embodiment of section 19 in FIG. 16;

FIGS. 20B–22B are cross-sectional views taken along lines 20B—20B, 21B—21B and 22B—22B, respectively, in FIG. 19B;

FIG. 19C is a detailed side view of a third embodiment of section 19 in FIG. 16;

FIGS. 20C–22C are cross-sectional views taken along lines 20C—20C, 21C—21C and 22C—22C, respectively, in FIG. 19C;

FIG. 25 is a plan view of a single operator exchange catheter in accordance with another embodiment of the present invention;

FIG. 26 is a detailed plan view of an entry region of one embodiment of the single operator exchange catheter of FIG. 25;

FIG. 27 is a partial perspective view of the catheter of FIG. 25 detailing a detachable hood;

DETAILED DESCRIPTION OF THE INVENTION

Figure 1B:
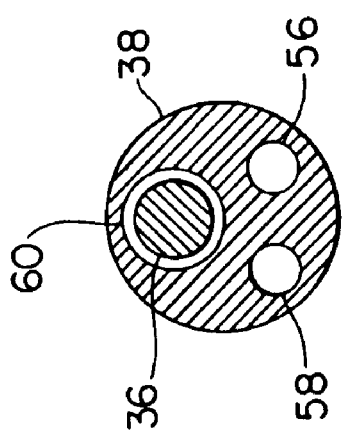
FIG. 1B is a cross-sectional view of the catheter with guidewire of FIG. 1 taken along the line B—B.

The following detailed description should be read with reference to the drawings in which similar elements in different drawings are numbered the same. The drawings, which are not necessarily to scale, depict selected preferred embodiments and are not intended to limit the scope or spirit of the invention.

FIG. 1 shows a perspective view of a catheter assembly 30 in accordance with the present invention. Catheter assembly 30 is used in catheter procedures for accessing targeted anatomical regions through the alimentary canal. The present invention incorporates features which allow rapid exchange of a catheter by a single operator. The catheter of the present invention allows shorter length guidewires to be used, resulting in procedures which require less medical personnel, are less time consuming, and less costly. Additionally, the present invention is adaptable to most catheter devices used for catheter procedures within the alimentary canal.

Catheter assembly 30 includes a catheter hub assembly 32 and a catheter 34, having a guidewire 36 passing through a portion thereof. Catheter 34 includes a shaft 38, which in general terms has a proximal end 40, a U-channel 42, a distal tip region 44, a distal end 46 and various lumens described in greater detail below. Catheter hub assembly 32 is operably connected to proximal end 40 of shaft 38. Catheter hub assembly 32 is preferably configured to couple to ancillary devices allowing access to a lumen within shaft 38.

Shaft 38 is a generally tubular shaped member having a generally uniform outer shape at proximal end 40. Shaft 38 may be sized for slidable passage through the lumen of an endoscope (not shown). Shaft 38 is preferably formed in an extrusion process. Shaft 38 may be formed of an extruded polymeric material. In one embodiment, the preferred polymeric material is polytetrafluoroethylene, polyether block amide, nylon or a combination or blend of these. Catheters which are contemplated include, but are not limited to, cannulas, sphincterotomes, cytology devices, and devices for stone retrieval and stent placement.

In a preferred embodiment, shaft 38 further includes a distal taper 48 which tapers to distal tip region 44. Additionally, tip region 44 may include high contrast, color coded distal markers 50. Finally, distal end 46 may be radiopaque for fluoroscopic visualization of distal tip region 44 during a catheter procedure.

U-channel 42 of shaft 38 extends between a first, proximal channel end 52 and a second, distal channel end 54. U-channel 42 serves to contain, but not necessarily constrain, guidewire 36, between channel proximal end 52 and channel distal end 54. The term "U-channel" refers to a channel shape that allows radial removal of guidewire 36 from the channel 42, and need not be strictly in the shape of the letter U. Channel 42 in the preferred embodiment is sufficiently large to allow unhindered radial guidewire 36 movement out of channel 42. Further, the channel walls and radial opening are substantially equal to or slightly larger than the diameter of a guidewire lumen, described in greater detail below. Although it is recognized that proximal channel end 52 may be located at any location distal of proximal end 40 of shaft 38, channel distal end 54 is preferably located between 10 and 40 cm from distal end 46 of catheter shaft 38.

Figure 1A:
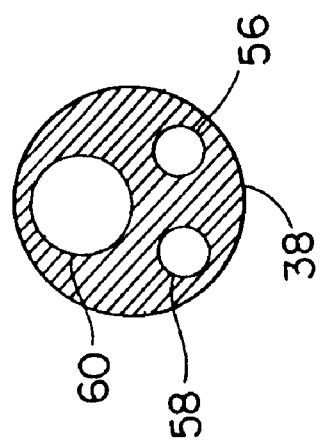
FIG. 1A is a cross-sectional view of the catheter of FIG. 1 taken along the line A—A.

Finally, as shown in FIG. 1A, which is a cross-sectional view of shaft 38 taken along line A—A at a location proximal of channel proximal end 52, shaft 38 includes ancillary lumen 56, ancillary lumen 58 and guidewire lumen 60.

Ancillary lumen 56 and ancillary lumen 58 extend longitudinally between proximal end 40 and distal end 46 of shaft 38. Ancillary lumen 56 and ancillary lumen 58 may be injection lumens, allowing for high contrast media flow capability for bubble-free opacification and for excellent visualization of a desired anatomical region. Additionally or alternatively, ancillary lumen 56 and/or ancillary lumen 58 may be used for or as part of other ancillary devices, such as a cutting wire lumen or a retrieval balloon lumen.

Guidewire lumen 60 extends longitudinally between proximal end 40 and distal end 46 of shaft 38 in the preferred embodiment. Further, guidewire lumen 60 is sized to receive guidewire 36. Guidewire lumen 60 may be a tubular member which is extruded integral catheter shaft 38, or alternatively, guidewire lumen 60 may be a separate tubular member which is coupled to catheter shaft 38. Although in one preferred embodiment the guidewire lumen 60 is a tubular member which is located proximate distal end 46 of catheter shaft 38, it is recognized that guidewire lumen 60 may be formed anywhere along shaft 38, may be an extension of shaft 38 coupled to distal end 46, or guidewire lumen 60 may run the entire length of shaft 38.

Referring to FIG. 1B, a cross-sectional view of shaft 38 taken along line B—B of FIG. 1 is shown. Guidewire 36 may access guidewire lumen 60 at a point proximal channel distal end 54. Guidewire 36 extends within channel 42 to channel distal end 54, continuing within guidewire lumen 60 through distal tip region 44, and exiting through an opening in distal end 46.

Referring to FIG. 1C, a section of catheter shaft 38 having U-channel 42 is shown. The embodiment shown also includes ancillary lumens 56 and 58. Sections of shaft 38 proximate the channel proximal end 52 and distal channel distal end 54 contain guidewire lumen 60 in communication with U-channel 42. In one embodiment, U-channel 42 has an interior, closed-side geometry, substantially the same as the geometry of guidewire lumen 60. Further, U-channel 42 walls are spaced further than a diameter of guidewire 36 such that guidewire 36 moves freely into and out of U-channel 42.

Catheter shaft 38 can be configured such that U-channel 42 is defined separately from guidewire lumen 60. With this approach, guidewire lumen 60 is divided into two sections; a first section extending between proximal end 40 of shaft 38 and channel proximal end 52; and a second portion extending between channel distal end 54 and distal end 46 of shaft 38. Alternatively, the shaft can be configured to define guidewire lumen 60 as extending longitudinally between proximal end 40 and distal end 46 of shaft 38. In the alternative embodiment, between channel proximal end 52 and channel distal end 54, guidewire lumen 60 is integral with U-channel 42. In other words, guidewire lumen 60 defines a portion of U-channel 42 such that spacing between outer walls of U-channel 42 is equal to a diameter of guidewire lumen 60. Regardless of how guidewire lumen 60 and U-channel 42 are defined, U-channel 42 provides for access to guidewire lumen 60 at channel distal end 54. In this regard, channel distal end 54 can be enlarged to more easily direct guidewire 36 into guidewire lumen 60.

Guidewire lumen 60 and U-channel 42 allow rapid exchange of catheter assembly 30 when an alternative catheter is necessary during a certain medical procedure. Shorter length guidewires may be used since guidewire 36 does not pass through shaft proximal end 40 and hub assembly 32, but rather exits the catheter shaft 38 at U-channel 42 located substantially distal from proximal end 40. The unique catheter construction in accordance with the present invention will reduce catheter therapeutic and diagnostic procedure time since catheter device exchanges may be performed relatively more easily and quickly by a single operator. Additional personnel and time associated with maintaining the placement of a conventional (approximately 400 cm) guidewire within the targeted anatomical region is eliminated, reducing the overall costs of the procedure.

Figure 1E:
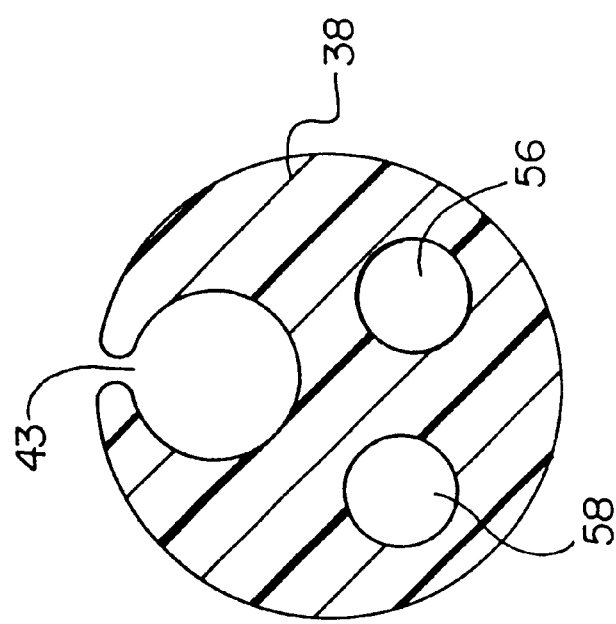
FIGS. 1D and 1E are cross-sectional views of the fragment illustrated in FIG. 1C.
Figure 1D:
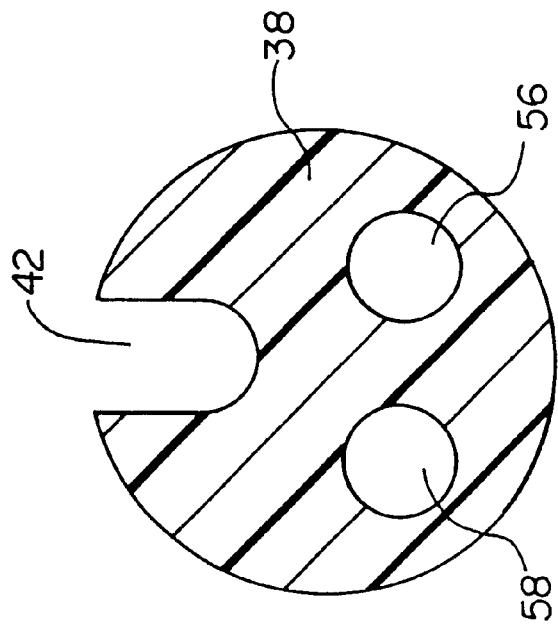

Referring now to FIGS. 1D and 1E, which are cross-sectional views of the shaft 38 fragment illustrated in FIG. 1C. Specifically, FIG. 1D is a precise cross-sectional view of the shaft 38 fragment illustrated in FIG. 1C, and FIG. 1E is an alternative cross-sectional view of the shaft 38 fragment illustrated in FIG. 1C. As described previously and now with reference to FIG. 1D, catheter shaft 38 includes a U-channel 42, a first ancillary lumen 56 and a second ancillary lumen 58. In this embodiment, U-channel 42 collectively defines a guidewire lumen and an opening providing access to the guidewire lumen. Similarly, in the embodiment illustrated in FIG. 1E, C-channel 43 collectively defines a guidewire lumen and a narrower opening for accessing the guidewire lumen. The narrower opening of C-channel 43 may have a dimension of approximately 0.018 inches and is designed to better contain the guidewire therein. C-channel 43 may eliminate the need for a separate exchange sheath when using endoscopes with larger lumens.

Figure 2B:
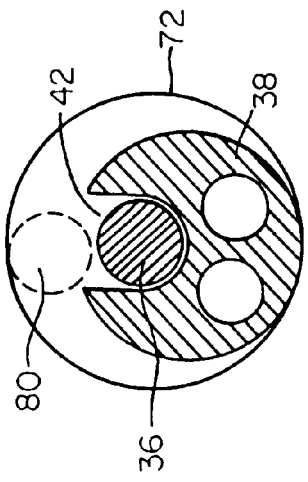
FIGS. 2A–2D are cross-sectional views of the catheter of FIG. 1 located within increasingly larger endoscope channels.
Figure 2D:
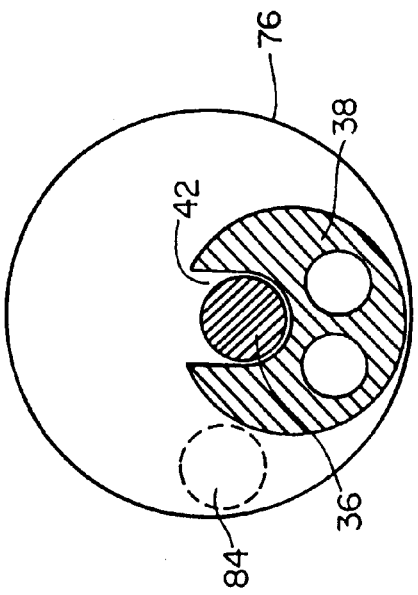
Figure 2A:
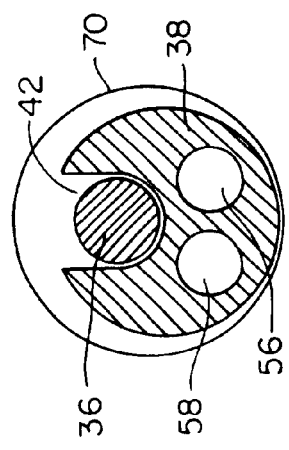

Referring to FIGS. 2A through 2D, cross-sectional views of endoscope working channels 70–76 containing a catheter according to FIG. 1 are shown. In the examples illustrated in FIGS. 2A through 2D, working channel inside diameters 70, 72, 74, and 76 are 2.8, 3.2, 3.8, and 4.2 mm; respectively. FIG. 2A illustrates catheter shaft 38 having ancillary lumens 56 and 58, U-channel 42, and guidewire 36 within U-channel 42. Further, shaft 38 is shown within a first size endoscope working channel 70. In FIG. 2A, guidewire 36 is effectively radially constrained by small sized working channel 70 that closely surrounds U-channel 42.

Figure 2C:
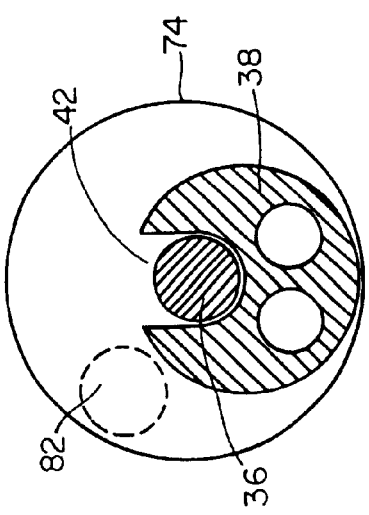

FIG. 2B illustrates catheter containment within a second size working channel 72, slightly larger than the working channel 70 of FIG. 2A. In FIG. 2B, guidewire 36 is able to move out of U-channel 42 to a position denoted with dashed lines at 80. FIG. 2C shows shaft 38 contained within a third, even larger sized working channel 74. Guidewire 36 is able to move completely out of U-channel 42 to position 82 shown with dashed lines. Finally, FIG. 2D demonstrates catheter shaft 38 within a fourth size working channel 76. In this even larger working channel, guidewire 36 lies within an even larger cross-sectional area, and is able to move to a position shown in FIG. 2D with dashed lines at 84.

As shown with the larger endoscope working channels (FIGS. 2C and 2D), the potential for guidewire 36 to slip out of U-channel 42 creates a potential for the guidewire 36 to become pinched and restrict desired movements of both guidewire 36 and catheter shaft 38. For this reason, when larger endoscope working channels are used, an exchange sheath having a sufficiently small inner diameter so as to constrain guidewire movement to within the catheter U-channel 42 is employed with one preferred embodiment. Generally speaking, an endoscope exchange sheath in accordance with one preferred embodiment allows for use of a radially accessible guidewire, which is longitudinally aligned with the catheter, while presenting a circular profile to an endoscope and mitigating guidewire pinching problems between the catheter and the endoscope working channel wall.

Referring to FIG. 3, an endoscope exchange sheath assembly 100 having sheath hub assembly 102 and a sheath 104 is shown. The sheath 104 includes a lumen 106 and a distal end 108. FIG. 3A shows a section of sheath 104, having lumen 106 for receiving a catheter. Basically, with reference to FIG. 1, catheter 34 is fed through lumen 106 of sheath 104 such that sheath 104 encompasses guidewire 36 within U-channel 42. Sheath 104 is adapted to be disposed within an endoscope working channel, thereby providing a smaller diameter channel than that of the surrounding endoscope working channel constraining the guidewire 34 (FIG. 1) to the U-channel 50 (FIG. 1), and mitigating the potential problems shown in FIGS. 2C and 2D.

Referring to FIG. 4, an alternate endoscope exchange sheath assembly 110 is shown. Sheath assembly 110 includes a two-piece hub assembly 112 and a sheath 114 defining lumen 116 and having slit 118 extending longitudinally over its length, terminating at distal end 120. Slit 118 in sheath 114 is shown in more detail in FIG. 4B.

Referring again to FIG. 4, two-piece hub assembly 112 has a proximal hub portion 122 and a distal hub portion 124, having a proximal slit 126 and a distal slit 128, respectively. Sheath slit 118 is in communication with hub slits 126 and 128, allowing a guidewire (not shown) to be radially slid into or out of sheath assembly 110. Proximal hub portion 122 is shown unlocked (position "A") in FIG. 4, aligning hub proximal slit 126 with hub distal slit 128 and sheath slit 118, providing a continuous slit for guidewire radial movement into and out of the sheath assembly 110. Proximal hub portion 122 is shown locked, in position "B", in FIG. 4A, whereby proximal hub slit 126 is rotated with respect to distal hub slit 128, preventing a guidewire (not shown) within hub assembly 112 from being moved radially out of hub assembly 112. Proximal hub portion 122 is set to position B (FIG. 4A) when radial guidewire movement is not desired.

FIG. 4C illustrates a portion of an alternate embodiment sheath 130 having a lumen 132, a sheath wall opening 134 and sheath wall overlap 136. A guidewire (not shown) is able to be slid out of lumen 132 of sheath 130 by maneuvering the guidewire into sheath wall opening 134 and through overlap 136.

Referring to FIG. 5, catheter assembly 30 depicted in FIG. 1 is shown inserted within endoscope exchange sheath assembly 110 depicted in FIG. 4. More particularly, catheter 34 is inserted through slitted sheath assembly 110, extending distally out sheath distal end 120. Guidewire 36 (shown partially in FIG. 5) is positioned within U-channel 42 of catheter 34, along guidewire lumen 60 (FIG. 1B), and extends from shaft distal end 46. Further, guidewire 36 is engaged by hub assembly 112. More particularly, guidewire 36 passes within and is engaged by proximal slit 126 and distal slit 128 of hub assembly 112. Sheath proximal hub portion 122, having proximal slit 126, is shown in locked position relative to sheath distal hub portion 124, having distal slit 128. Thus, in the locked position, hub assembly 112 of sheath assembly 110 prevents radial withdrawal of guidewire 36, otherwise inserted in U-channel 42 of catheter 34, from distal the channel proximal end 52.

Referring to FIG. 6, a section of FIG. 5 is shown in detail, having endoscope sheath 114 containing catheter shaft 38, which further maintains guidewire 36 within U-channel 42. As shown, sheath 114 is able to constrain movement of guidewire 36 from U-channel 42 when sheath 114 is within a larger endoscope working channel, for example as illustrated in FIGS. 2C and 2D. Importantly, the sheath 114 embodiment illustrated in FIG. 6 includes longitudinal slit 118, allowing guidewire 36 to be peeled from catheter shaft 38 and endoscope sheath 114. In other words, as previously described, U-channel 42 is sized larger than guidewire 36 such that guidewire 36 can displace radially from U-channel 42. Sheath 114 prevents undesired displacement of guidewire 36 from U-channel 42 under normal operating conditions. However, if adequate radial force is placed on guidewire 36 by an operator, guidewire 36 will separate sheath 114 along slit 118 such that guidewire 36 is displaced from sheath 114 and U-channel 42.

Referring to FIG. 7, guidewire 36 is shown inserted within catheter assembly 30 of FIG. 1, which is inserted through endoscope sheath assembly 110 of FIG. 4, which is in turn within an endoscope 150. Sheath assembly 110 includes sheath 114 that has slit 118 and two-piece hub assembly 112, shown at a locked position "B" (also in FIG. 4A). Having hub assembly 112 locked prevents guidewire 36 from moving radially out of sheath 114 through slit 118. Guidewire 36 can be restrained from longitudinal movement by applying finger pressure on the guidewire 36 against hub assembly 112.

Referring to FIG. 7A, endoscope 150 and sheath assembly 110 of FIG. 7 are shown without the catheter assembly 30 inserted, as after catheter withdrawal. Sheath hub assembly 112 is shown in unlocked position at "A" (also in FIG. 4). Having hub assembly 112 unlocked allows radial movement of guidewire 36 out of sheath 114 through slit 118, but such movement may be restrained by trapping guidewire 36 against the outside of sheath 114 using one finger, providing ease of guidewire 36 control during catheter exchanges.

In one possible endoscopic procedure, an endoscope 150, as illustrated in FIG. 7, is first introduced into the mouth of a patient and is guided through the patient's alimentary canal. Specifically, endoscope 150 is guided down the esophagus, through the stomach, past the pyloric sphincter of the stomach and into the duodenum. Endoscope 150 has a lumen extending longitudinally between its proximal end and the distal end.

Endoscope 150 is guided through the alimentary canal until a distal end (not shown) of endoscope 150 is proximate the target area within the anatomy to receive treatment. In an endoscopic biliary procedure, endoscope 150 is guided into the duodenum until the opening at the distal end of the endoscope 150 is proximate the papilla of vater. The papilla of vater is located between the sphincter of oddi, which leads to the common bile duct, hepatic, and pancreatic ducts. The proximal end (shown in FIGS. 7 and 7A) of endoscope 150 extends and remains outside the mouth of the patient.

With endoscope 150 properly positioned within the patient, catheter assembly 30 is prepared for insertion into the endoscope. First, guidewire 36 is fed into the guidewire lumen 60 (FIGS. 1A–1C) of shaft 38. More particularly, a distal end of guidewire 36 is placed within U-channel 42, distal the channel proximal end 52. The guidewire 36 is then fed to channel distal end 54 (FIG. 1) into guidewire lumen 60. Finally, guidewire 36 is fed through shaft 38 to distal tip region 40 (FIG. 1). In one method, catheter 32 is then inserted directly into endoscope 150 working channel. This method may be practiced with an endoscope having a sufficiently small working channel inside diameter, as illustrated in FIG. 2A, to constrain guidewire 36 movement without a sheath.

However, in a preferred method (with reference to FIG. 7), catheter assembly 30, threaded with guidewire 36, is inserted into sheath assembly 110, thereby constraining guidewire 36 from slipping radially out of U-channel 42. More particularly, catheter 34 is inserted into endoscope 150 working channel, but leaving channel proximal end 52 proximate sheath hub assembly 112, and leaving a portion of guidewire 36 extending from the channel proximal end 52 as well. Notably, sheath hub assembly 112 includes hub slits 126 and 128 which receive a portion of guidewire 36. Thus, in the preferred embodiment, hub assembly 112 is locked, preventing unwanted radial guidewire 36 movement. In a preferred method, the loading of guidewire 34 into catheter shaft 38 and catheter shaft 38 into sheath assembly 110 is done prior to inserting endoscope 150 into a patient (not shown).

Endoscope sheath 114, containing catheter shaft 38, is inserted into endoscope 150 working channel. Endoscope sheath 114 serves to constrain radial guidewire 36 movement over the approximate length of U-channel 42. Catheter shaft 38 and sheath 114 are inserted together into endoscope 150 until both are near a distal end (not shown) of endoscope 150. Catheter shaft 38 and sheath 114 may be, either or both, advanced until exiting the distal end of endoscope 150.

In one method, guidewire 36 is advanced until guidewire 36 distal tip is positioned within the target area in the biliary tree (including the common bile, hepatic or pancreatic ducts). For example, the distal tip of guidewire 36 may be guided through the orifice leading to the papilla of vater for access to the biliary tree. Catheter shaft 38 may then be advanced over guidewire 36, tracking catheter assembly 30, until catheter distal tip region 40 (FIG. 1) exits distal end of endoscope 150 and is positioned within the desired duct. In another method, guidewire 36 and catheter assembly 30 are advanced together until catheter distal end 42 (FIG. 1) is positioned at the target area. It is also recognized that the catheter could be first advanced to near the target area, followed by inserting the guidewire when needed to advance the catheter further.

Once guidewire 36 is in position at the target area, catheter procedures, including injecting contrast media, such as radiopaque dye, through ancillary lumens 56 or 58 (FIGS. 1A–1C) into the common bile duct for visualization of the duct, can be performed. After the desired catheter procedure has been completed, catheter assembly 30 can be exchanged or removed from endoscope 150, leaving guidewire 36 in position for other catheter procedures. Catheter assembly 30 and sheath assembly 110 may also be removed together.

One method of withdrawing catheter 34 from endoscope 150 is possible using either a slitted/overlapped endoscope sheath 114 as depicted in FIGS. 4 through 4C, or a sheath 104 without a slit as depicted in FIGS. 3 through 3A. Using this method, best visualized with reference to FIG. 7, guidewire 36 is held to prevent longitudinal movement while catheter 34 is retracted within endoscope sheath 114 (or 104). Catheter 34 retraction leaving the guidewire 36 in position within the patient is enabled by U-channel 42 being radially open to guidewire 36 removal in catheter shaft 36. Once catheter retraction has brought channel distal end 54 (FIG. 1) to a point proximate sheath hub assembly 112, only a relatively short portion of guidewire 36, from channel distal end 54 to distal end 46 (FIG. 1) of catheter shaft 38, remains within catheter 34. A single operator can remove this remaining portion of guidewire 36 from catheter 34 by first slightly retracting catheter assembly 30 (while still holding guidewire 34 in place) out of sheath assembly 110 (or 100), such that a portion of guidewire 36 is accessible distal of catheter distal end 46. In other words, a small portion of guidewire 36 is accessible between distal end 46 of catheter 34 and distal hub portion 124 of sheath assembly 110. The accessible portion of guidewire 36 is then held by the operator, while withdrawing the remaining portion of catheter 34 completely over guidewire 36. In an alternative method, the distal end of the endoscope can include an elevator which could be utilized to lock the distal end of the guidewire in position while the catheter is removed.

Exchange of endoscope sheath assembly 110 may be desired, as when a stent (not shown) is to be advanced over guidewire 36, and the stent has a larger outside diameter than can be accommodated by the sheath 114. One method of exchanging an endoscope sheath assembly 110 may be used where sheath 114 is slitted as in FIG. 4B, or overlapped, as in sheath 130 in FIG. 4C. Referring to FIG. 7A, two-piece hub assembly 112 is turned to the unlocked position "A" (also shown in FIG. 4). Guidewire 36 is pulled radially away from sheath hub assembly 112 and through slit 118 in sheath 114. Guidewire 36 is then held, preferably against some portion of endoscope 150, to prevent guidewire 36 from being dislodged from position within the patient. Sheath 114 is retracted from endoscope 150, guidewire 36 being "peeled" away from sheath 114. Sheath retraction is continued until sheath 114 is completely outside of endoscope 150 and over guidewire 36. At this point, guidewire 36 is within endoscope 150 working channel, and stents, catheters, and endoscope sheaths may be advanced over guidewire 36.

Another method of exchanging both endoscope sheath assembly 110 and catheter assembly 30 may be used where the sheath 114 is slitted as in FIG. 4B, or overlapped, as in sheath 130 in FIG. 4C. Referring to FIGS. 7 and 7A, two-piece hub assembly 112 is turned to the unlocked position "A" (FIG. 7A). Guidewire 36 is pulled radially away from U-channel 42 of catheter 34, from hub assembly 112 and through slit 118 in sheath 114. Guidewire 36 is then held, preferably against some portion of endoscope 150, to prevent guidewire 36 from being dislodged from position within the patient. Sheath 114 and catheter 34 are retracted from endoscope 150, with guidewire 36 being "peeled" away from sheath 114. Sheath assembly 110 and catheter assembly 30 retraction are continued until sheath 114 and catheter 34 are completely outside of endoscope 150 and over guidewire 36. At this point, guidewire 36 remains in a position within endoscope 150 and patient. A single operator can access a small portion of guidewire 36 between distal end 46 (FIG. 1) of catheter 34 to hold guidewire 36 in place while catheter assembly 30 is completely removed or disengaged from guidewire 36.

While sheath assembly 110 has been described as including a two-piece hub assembly 112 in conjunction with sheath 114, other assemblies may be used. For example, referring to FIG. 8, an alternate sheath assembly 160 is shown. Sheath assembly 160 includes an introducer 162, an attachment means 164 and a sheath 166. Similar to previous embodiments, sheath 166 defines a lumen (not shown) and includes a slit 168 extending longitudinally over its length, terminating at a distal end 170. Sheath 166 is generally identical to sheath 104 and sheath 114 previously described. Introducer 162 is attached to sheath 166 by attachment means 164 such that lumen (not shown) of sheath 166 is in fluid communication with an interior portion of introducer 162. In one preferred embodiment, attachment means 164 is a flexible membrane which seals sheath 166 to introducer 162. Alternatively, other forms of attachment, such as an adhesive or frictional engagement between introducer 162 and sheath 166 may also be useful.

Referring to FIG. 8A, introducer 162 is shown in greater detail. Introducer 162 is a funnel-shaped device including a horn 172 and a neck 174. In one preferred embodiment, horn 172 and neck 174 are integrally formed as a singular body.

Horn 172 is preferably a conically-shaped body having an outer wall 176. Outer wall 176 defines an interior space and includes a guidewire-receiving notch 180 formed near proximal end 182 of horn 172. Guidewire-receiving notch 180 is preferably J-shaped and includes an entry end 184 and a locking end 186. As shown in FIG. 8A, entry end 184 is open at proximal end 182 of horn 172. Conversely, locking end 186 is closed.

Neck 174 is preferably tubular in shape, and includes a passage 188. Passage 188 is configured to be in fluid communication with interior space of horn 172. In the preferred embodiment, horn 172 and neck 174 are formed of a plastic material. Alternatively, any other semi-rigid or rigid, surgically-safe material may be used.

Referring to FIGS. 1, 8 and 8A, during use, catheter assembly 34 (FIG. 1) is inserted within sheath assembly 160. More particularly, distal end 46 (FIG. 1) of catheter shaft 38 (FIG. 1), including guidewire 36 (FIG. 1) is placed within horn 172 of introducer 162. The conical shape of horn 172 assists in directing distal end 46 of catheter shaft 38, including guidewire 36, into passage 188 of neck 174. Catheter shaft 38 continues forward within lumen (not shown) of sheath 166 until distal end 46 of catheter shaft 38 extends from distal end 170 of sheath 166.

Once properly inserted within sheath assembly 160, a proximal end of guidewire 36 (FIG. 1) is maintained within guidewire-receiving notch 180. More particularly, a portion of guidewire 36 is forced by an operator through entry end 184 of guidewire-receiving notch 180 and forced within locking end 186 thereof. In this regard, locking end 186 preferably has a diameter slightly smaller than that of guidewire 36. Thus, locking end 186 frictionally maintains guidewire 36. Conversely, guidewire 36 can easily be released from guidewire-receiving notch 180 by sliding guidewire 36 from locking end 186 and out of entry end 184. Thus, sheath assembly 160 functions in a manner highly similar to sheath assembly 100 and sheath assembly 110 previously described.

Referring to FIG. 9A, an alternative embodiment of an introducer 190 is shown. Introducer 190 includes a horn 192, a neck 194 and a valve 196. Similar to previous embodiment, horn 192 and neck 194 are preferably integrally formed as a singular body. Horn 192 includes an outer wall 197 which defines a guidewire-receiving notch 198 and valve-receiving slots 200. Valve 196 includes a valve body 202 sized to fit within outer wall 197 of horn 192. Further, valve 196 includes ribs 204 extending from valve body 202.

Ribs 204 are preferably sized to mate within valve-receiving slots 200 of horn 192. Thus, valve 196 is maintained within horn 192 via interaction of ribs 204 with valve-receiving slots 200. In this regard, valve-receiving slots 200 are preferably positioned along horn 192 proximal neck 194. Valve 196 is preferably made of a rubber-type material.

During use, introducer 190 functions in a manner highly similar to introducer 162 (FIGS. 8 and 8A) previously described. Additionally, however, valve 196 forms a seal about catheter shaft 38 (FIG. 1). Thus, upon insertion into a human body, valve 196 prevents bodily fluids, such as bile, from backing up through the sheath assembly. Additionally, valve 196 can provide for aspiration, if desired.

Referring to FIG. 9B, an alternative embodiment of an introducer 206 is shown. Introducer 206 is highly similar to introducer 190 (FIG. 9A) previously described. In this regard, introducer 206 includes a horn 208, a neck 210 and a valve 212. Horn 208 is preferably integrally formed with neck 210 and includes an outer wall 214 defining a guidewire-receiving notch 216 and valve-receiving slots 218. Similar to valve 196 (FIG. 9A), valve 212 includes a valve body 220 and ribs 222. Ribs 222 are sized to mate within valve-receiving slots 218 of horn 208. In this regard, valve-receiving slots 218 are positioned proximate a proximal end 224 of horn 208. Introducer 206, including valve 212, functions in a manner highly similar to introducer 190 (FIG. 9A) as previously described.

It is recognized that the fluid blocking function provided by valve 212 can be achieved with other designs. For example, referring to FIG. 9C, an alternative embodiment of an introducer 226 is shown. Introducer 226 includes a horn 228, a neck 230 and an O-ring 232. Horn 228 and neck 230 are preferably formed as an integral body. Horn 228 preferably includes a guidewire-receiving notch (not shown) similar to that previously described and an interior slot 234. Interior slot 234 is preferably positioned proximate neck 230 and is sized to maintain O-ring 232. Alternatively, interior slot 234 can be formed in neck 230.

O-ring 232 is preferably made of a rubber-type material. Further, O-ring 232 has an inner diameter slightly smaller than that of horn 228 and neck 230. Thus, during use, O-ring 232 forms a seal about catheter shaft 38 (FIG. 1), blocking passage of bodily fluids, such as bile, into horn 228.

Referring to FIG. 9D, another alternative embodiment of an introducer 236 is shown. Introducer 236 is similar to a touhey-borst system and includes an upper horn section 238, a lower horn section 240 and a grommet 242. Upper horn section 238 includes an outer wall 244 defining a proximal end 246, a grommet-receiving flange 248 and a distal end 250. Proximal end 246 of horn section 238 preferably includes a guidewire-receiving notch (not shown) similar to that previously described. Distal end 250 is threaded and includes a passage 252 sized to receive a portion of lower horn section 240.

Lower horn section 240 includes a body 254 defining a proximal end 256, an intermediate portion 258 and a distal end 260. An interior passage 266 is configured to communicate with passage 252 and extends from proximal end 256 to distal end 260. Finally, proximal end 256 includes a threaded slot 262 sized to threadably receive distal end 250 of upper horn section 238.

Grommet 242 is preferably made of a rubber-type material and is sized to nest within grommet-receiving flange 248 of upper horn section 238 while abutting proximal end 256 of lower horn section 240.

Introducer 236 is assembled by placing grommet 242 within grommet-receiving flange 248 of upper horn section 238. Distal end 250 of upper horn section 238 is then threadably secured to proximal end 258 of lower horn section 240. As upper horn section 238 is threadably secured to lower horn section 240, proximal end 256 of lower horn section 240 compresses grommet 242 within grommet-receiving flange 248 of upper horn section 238. During use, introducer 236 functions in a manner highly similar to that previously described. In this regard, grommet 242 forms a seal about catheter shaft 38 (FIG. 1). Further, aspiration can be achieved, if desired, by loosening lower horn section 240 relative to upper horn section 238.

Referring to FIG. 9E, yet another alternative embodiment of an introducer 266 is shown. Introducer 266 includes a horn 268, a neck 270 and a valve 272. Preferably, horn 268, neck 270 and valve 272 are integrally formed as a singular body. In this regard, valve 272 is formed while molding horn 268 and neck 270 by imparting a controlled flash at distal end 274 of neck 270.

Introducer 266 performs in a manner highly similar to that previously described. Thus, valve 272 forms a seal about catheter shaft 38 (FIG. 1), thereby preventing back flow of bodily fluids, such as bile, into horn 268.

Referring to FIG. 9F, another alternative embodiment of an introducer 276 is shown. Introducer 276 includes a horn 278, a neck 280 and a valve 282. Horn 278 and neck 280 are preferably integrally formed as a singular body. In this regard, horn 278 and neck 280 are defined by an outer wall 284. Outer wall 284 forms a guidewire-receiving notch 286 and an exterior slot 288. Guidewire-receiving notch 286 is similar to that previously described. Exterior slot 288 is positioned along neck 280 and is sized to maintain a portion of valve 282. Alternatively, exterior slot 288 can be positioned along horn 278.

Valve 282 is preferably a rubber-type sock defined by an upper rib 290, a side wall 292 and a shoulder 294. Upper rib 290 is preferably sized to mount within exterior slot 288 of neck 280. Side wall 292 is preferably flexible so as to stretch along neck 280. Finally, shoulder 294 is preferably configured to abut a distal end 298 of neck 280. With this configuration, valve 282 is placed over distal end 298 of neck 280 such that shoulder 294 contacts distal end 298. Due to the preferred flexible characteristic of valve 282, side wall 292 is stretched until upper rib 290 nests within exterior slot 288 of neck 280.

During use, the catheter shaft 38 (FIG. 1) is placed through introducer 276 such that shoulder 294 of valve 282 forms a seal about catheter shaft 38. Thus, valve 282 prevents undesired back flow of bodily fluids, such as bile.

FIG. 10 is a perspective view of an illustrative locking device for use with an endoscope having a side instrument port. The illustrative locking device is generally shown at 320 and includes a body member 322. At one end, the body member 322 includes one or more hook members 324 for attaching the locking device to a shaft of an endoscope or the like (see FIG. 11). At the other end, the body member 322 includes a securing mechanism for securing a guidewire or catheter to the locking device.

Figure 13:
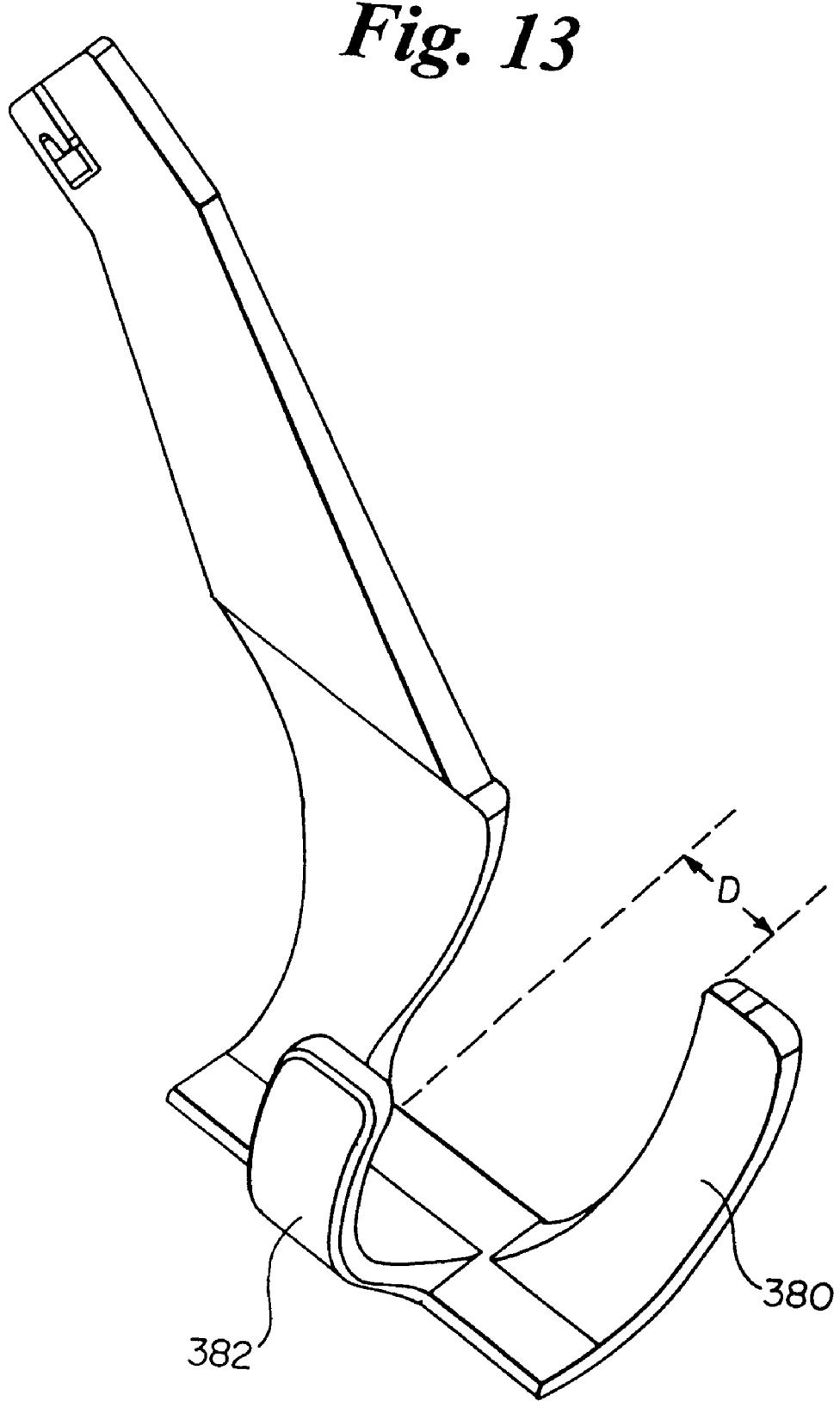
FIG. 13 is a perspective view of another illustrative locking device.

The hook members 324 may be provided in pairs, as shown in FIG. 10, or offset from one another, as shown in FIG. 13. In either case, the hook members 324 are adapted to clip and secure the locking device to the shaft of an endoscope or the like.

The securing mechanism preferably includes one or more openings provided in the body member 322. In the embodiment shown, the body member 322 includes a guidewire opening 326 and a catheter opening 332. The guidewire opening 326 is similar to the guidewire-receiving notch 180 of FIG. 8A. The guidewire opening 326 is preferably J-shaped, and preferably includes an entry slot 328 and a locking slot 330. The catheter opening 332 is boot shaped, and also preferably includes an entry slot 334 and a locking slot 336.

The entry slot 328 of the guidewire opening 326 is dimensioned to be larger than the diameter of a guidewire. The locking slot 330 of the guidewire opening 326 is dimensioned to be somewhat smaller than the diameter of a guidewire. Accordingly, a guidewire can be secured to the body member 322 by inserting a portion of the guidewire through the entry slot 328 of the guidewire opening 326 and into the locking slot 330. The locking slot 330 frictionally secures the guidewire relative to the body member 322.

Likewise, the entry slot 334 of the catheter opening 332 is dimensioned to be larger than the diameter of a catheter. The locking slot 336 of the catheter opening 332 is dimensioned to be somewhat smaller than the diameter of a catheter. Accordingly, a catheter can be secured to the body member 322 by inserting a portion of the catheter through the entry end 334 of the catheter opening 332 and into the locking slot 336. The locking slot 336 frictionally secures the catheter relative to the body member 322.

Figure 11:
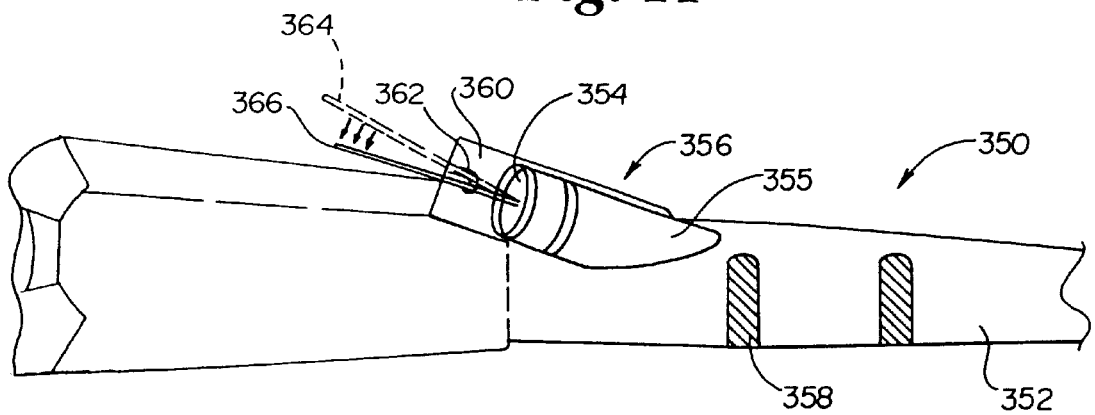
FIG. 11 is a partial side view of an illustrative locking device positioned on an endoscope having an angled side port.

FIG. 11 is a partial side view of an illustrative locking device positioned on an endoscope with an angled side port extending therefrom. The endoscope is generally shown at 350, and includes a main shaft 352 with a lumen extending therethrough. A side port 356 extends laterally away from the main shaft 352 at an angle. The side port 356 provides access to the lumen of the main shaft 352. Accordingly, a guidewire and/or catheter may access the lumen of the main shaft 352 via the side port 356.

The side port 356 preferably includes a side port opening 354 which is laterally spaced from the main shaft 352 due to the angular displacement between the main shaft 352 and the side port 356. The side port opening 354 is in fluid communication with the lumen of the main shaft 352 via a connection tube 355. The connection tube 355 intersects a side wall of the main shaft 352 at an angle, as shown.

A locking device having a body member 360 is shown clipped onto the main shaft 352 of the endoscope. The body member 360 includes a number of hook members 358 for attaching the locking device to the main shaft 352. Two hook members are visible in FIG. 11. The hook members 358 are similar to the hook members 324 described above with respect to FIG. 10.

The body member 360 extends away from the hook members 358 and generally parallel to the side port 356. In FIG. 11, the body member is obscured by the main shaft 352 and side port 356. The body member 360 extends upward past the side port opening 354, wherein a securing mechanism is provided. Preferably, the securing mechanism is a J-shaped guidewire opening 362.

In use, a guidewire is advanced into the body via the endoscope. During the advancement of the guidewire, the proximal end thereof may be moved to a first position 364, which is in the entry slot of the guidewire opening 362. Once the guidewire is in a desired position within the body, the guidewire may be moved to a second position 366, which is in the locking slot of the guidewire opening 362. The locking slot of the guidewire opening 362 frictionally secures the guidewire relative to the body member 360.

Figure 12:
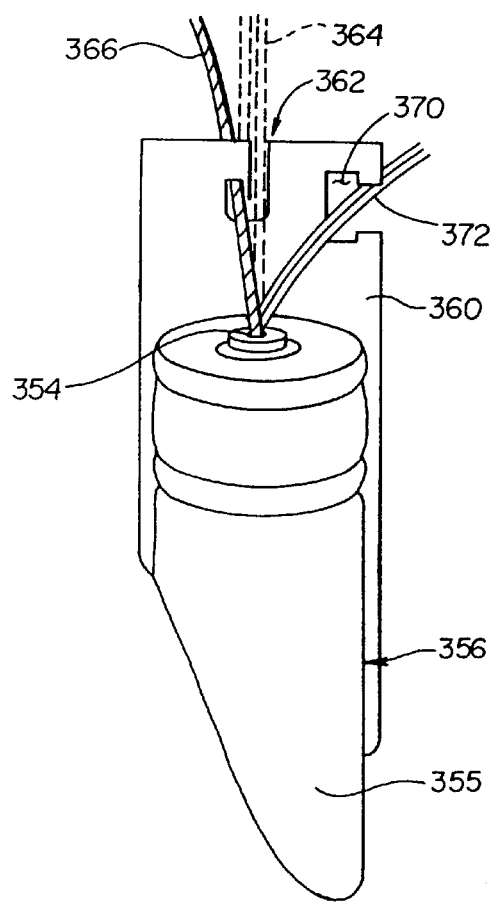
FIG. 12 is a partial side view detailing the illustrative locking device of FIG. 11.

FIG. 12 is a partial side view detailing the illustrative locking device of FIG. 11, with an additional oversized catheter opening shown. The side port of the endoscope is shown at 356, and the body member of the locking device is shown at 360. Positioned proximate the side port opening 354 is a guidewire opening 362 and an oversized catheter opening 370. Like above, the guidewire opening is J-shaped and includes an entry slot and a locking slot. Thus, the guidewire may be moved to the first position 364, which is in the entry slot of the guidewire opening 362. Once the guidewire is in a desired position within the body, the guidewire may be moved to the second position 366, which is in the locking slot of the guidewire opening 362. The locking slot of the guidewire opening 362 frictionally secures the guidewire relative to the body member 360.

The oversized catheter opening 370 is sized to restrict lateral movement of the catheter 372 but not longitudinal movement of the catheter 372. Providing a guidewire opening that can secure the guidewire relative to the body member, and an oversized catheter opening for only restricting lateral movement of the catheter 372 may be particularly useful in performing a catheter exchange procedure. For example, during a catheter exchange procedure, the guidewire opening may maintain the position of the guidewire. The oversized catheter opening 370 may separate the catheter from the guidewire, as the catheter is withdrawn. The first and second catheters should be single-operator exchange type catheters to provide access to the guidewire during the exchange.

FIG. 13 is a perspective view of another illustrative locking device. The embodiment shown in FIG. 13 is similar to the embodiment shown in FIG. 10, but the hook members are laterally offset rather than aligned. For example, hook member 380 is laterally offset from hook member 382 by a distance "D". This configuration is another example of an attachment mechanism for attaching the body member to a catheter shaft.

FIG. 14 is a perspective view of yet another illustrative locking device. The locking device is generally shown at 400, and includes a body member 401 having an attachment mechanism 402 at one end and a securing mechanism 404 at the other. The attachment mechanism 402 includes a first hook member 406 and a second hook member 408. The first hook member 406 and the second hook member 408 are adapted to extend around a substantial portion of the shaft of an endoscope or the like. Thus, the first hook member 406 and the second hook member 408 may clip the body member 401 to the desired shaft.

The securing mechanism 404 includes a J-shaped guidewire opening 410 and a flap-type catheter opening 412. The J-shaped guidewire opening 410 operates similar to that described above. The flap-type catheter opening 412 has a flap 414 formed by cutting the catheter opening 412 from the body member 401. The flap 414 is preferably curved to form a channel 416, wherein the end portion 418 of the channel 416 loops back to near the surface of the body member 401. In this configuration, a catheter or guidewire may be selectively provided in the channel 416, which may bend the flap away from the body member 401. Accordingly, the flap 412 may provide force between the guidewire or catheter and the body member 401 to effectively secure the guidewire or catheter to the body member 401.

FIG. 15 is a partial side view of yet another illustrative locking device 500. The locking device 500 is positioned between the side port 504 and the main shaft 506 of the endoscope 502. The locking device includes a body member 510 that is attached to the main shaft 506 using a strap 512. Preferably, the strap 512 extends around the entire circumference of the main shaft 506. Further, the body member 510 may include a guidewire opening 514 and one or more catheter openings 516, as shown.

Figure 16:
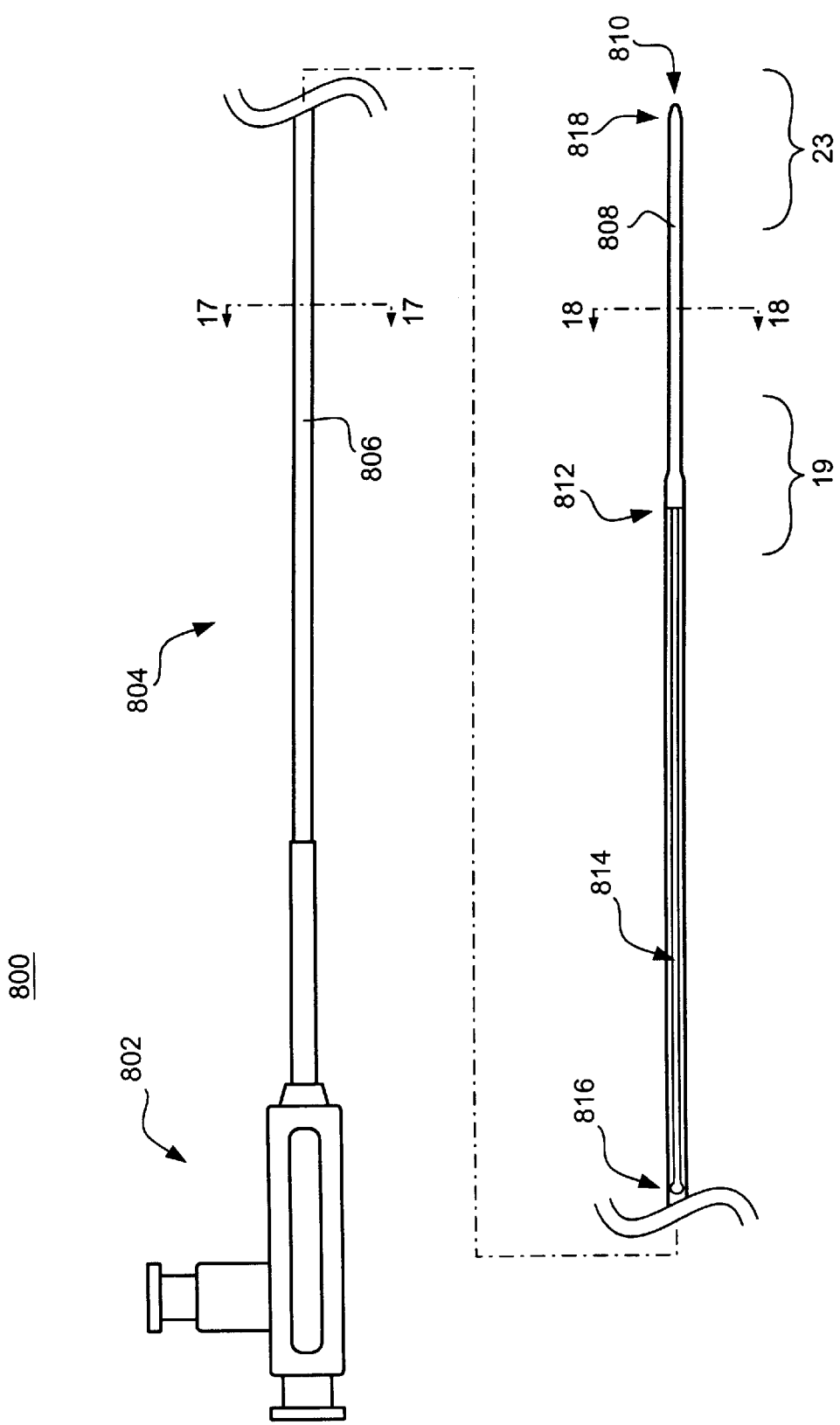
FIG. 16 is a side view of a single operator exchange catheter in accordance with another embodiment of the present invention.
Figure 18:
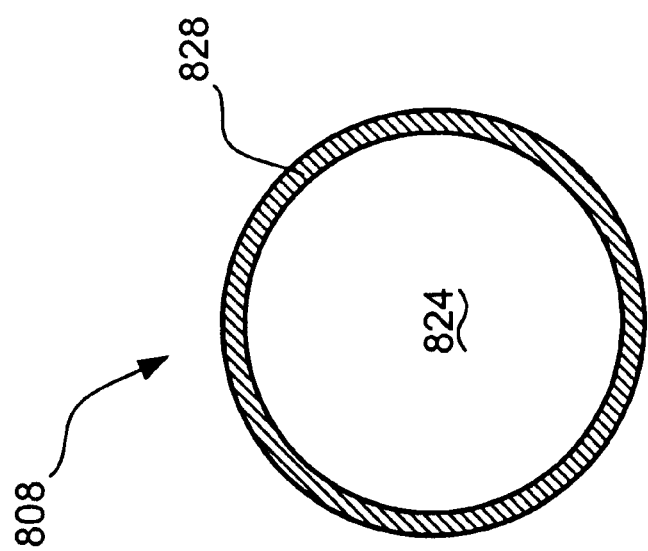
FIG. 18 is a cross-sectional view taken along line 18—18 in FIG. 16.
Figure 17:
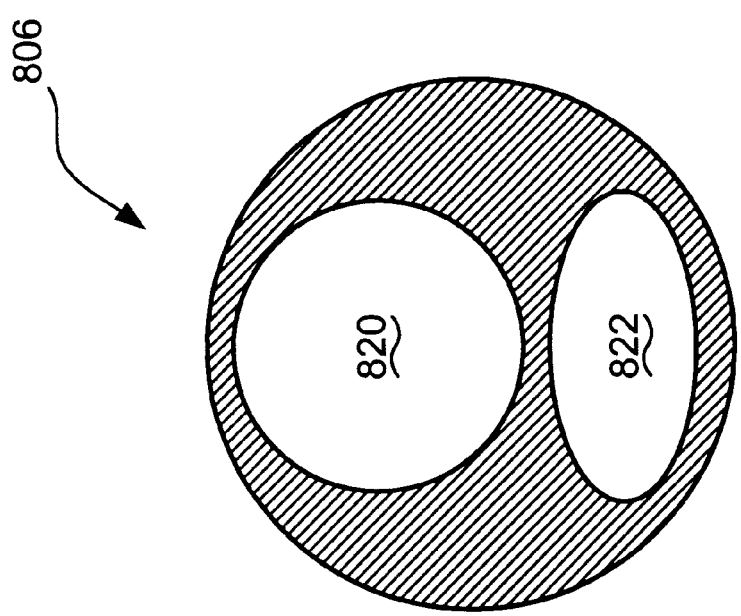
FIG. 17 is a cross-sectional view taken along line 17—17 in FIG. 16.
Figure 22A:
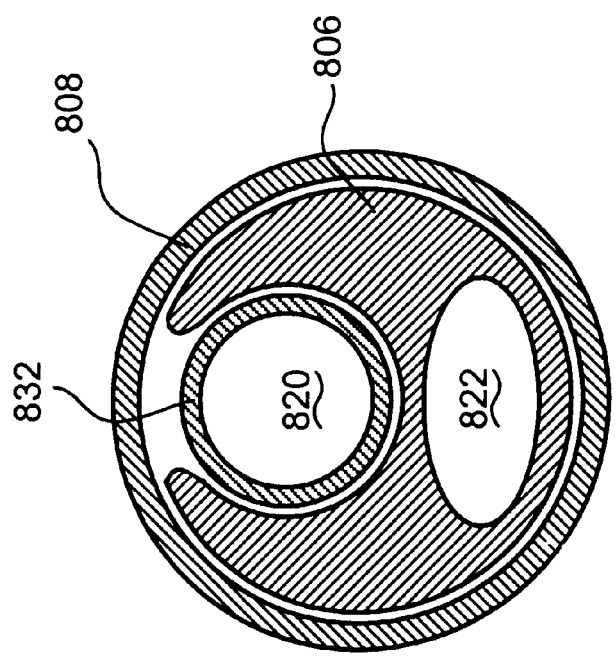
Figure 21A:
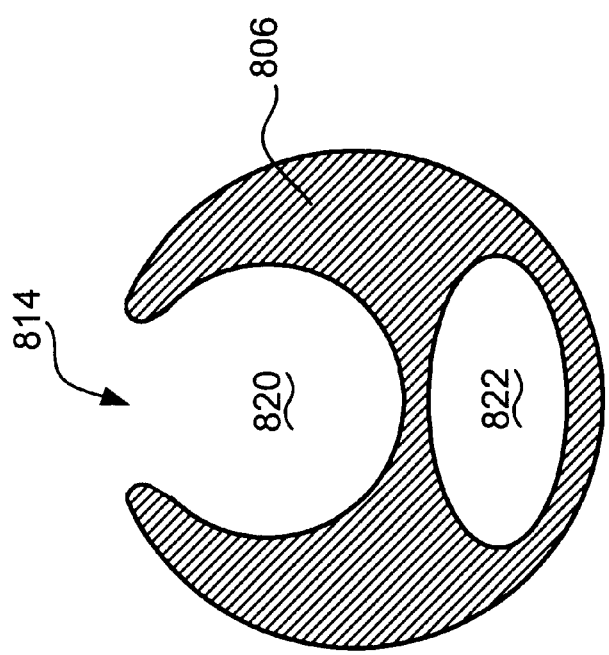
Figure 22B:
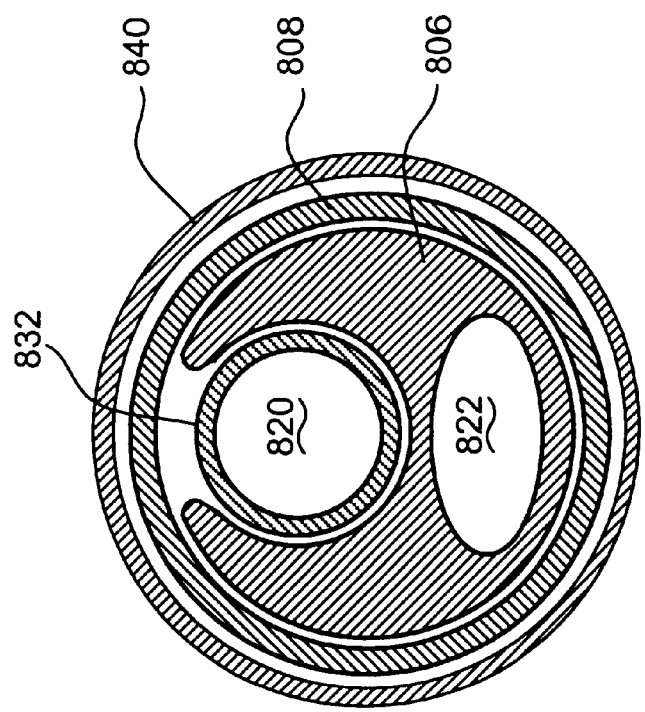
Figure 21B:
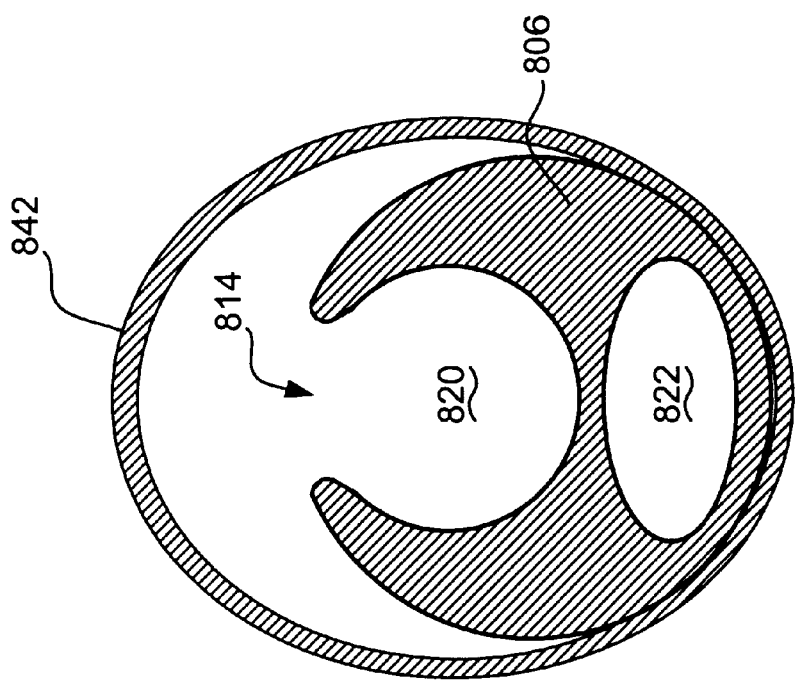
Figure 22C:
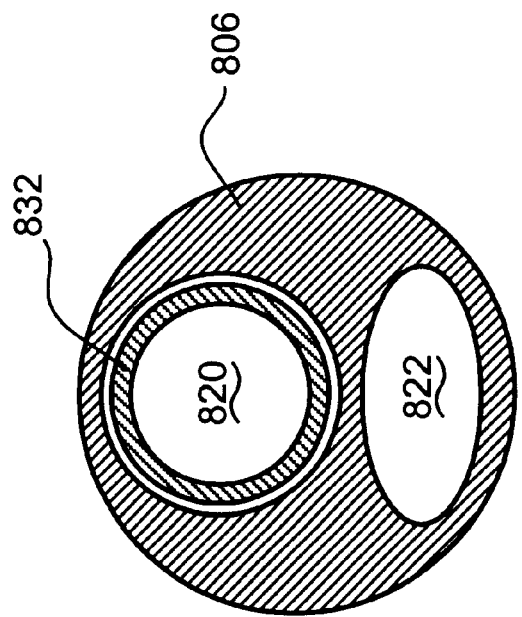
Figure 21C:
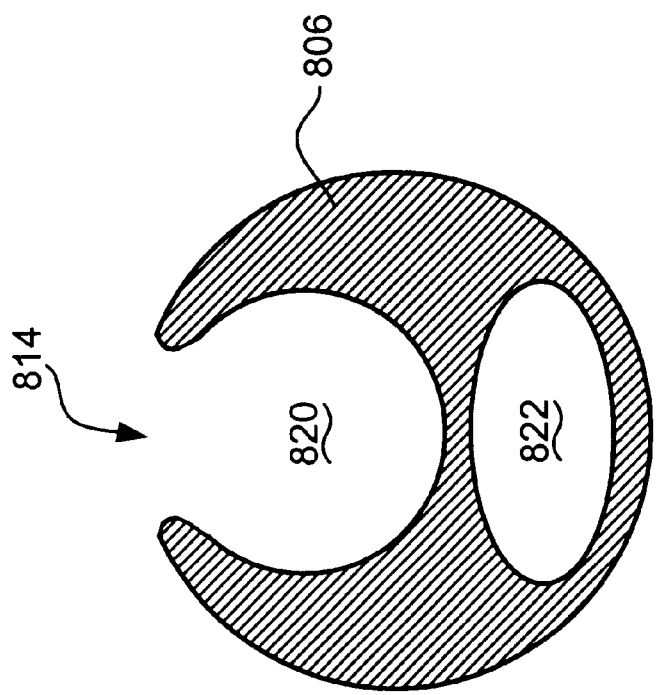

Refer now to FIG. 16, which illustrates a side view of a single operator exchange catheter assembly 800 in accordance with another embodiment of the present invention. Except as specifically described herein, catheter assembly 800 is the same in form and function as catheter assembly 30 described previously. Catheter assembly 800 includes a standard hub assembly 802 connected to the proximal end of an elongate shaft 804. Elongate shaft 804 includes a proximal portion 806 and a distal portion 808. Preferably, the proximal shaft portion 806 comprises a multi-lumen extrusion such as bitumen or tri-lumen tubing. Also preferably, the distal shaft portion 808 comprises a single lumen extrusion. A cross-sectional view of the proximal portion 806 of the elongate shaft 804 is illustrated in FIG. 17. Similarly, a cross-sectional view of the distal portion 808 of the elongate shaft 804 is illustrated in FIG. 18. The various embodiments of the junction between the proximal shaft portion 806 and the distal portion 808 are discussed in more detail with reference to FIGS. 19A–19C. In addition, the various distal tip 818 embodiments of the distal shaft portion 808 are discussed in more detail with reference to FIGS. 23A–23C. Common features of each embodiment are discussed in detail with reference to FIGS. 16, 17, and 18.

Catheter assembly 800 includes a distal guidewire port 810 disposed at the distal end of the distal shaft portion 808. A proximal guidewire port 812 is disposed adjacent the proximal end of the distal shaft portion 808. The proximal guidewire port 812 may be disposed along any portion of the shaft 804 distal of the hub assembly 802 and proximal of the distal guidewire port 810. Preferably, the proximal guidewire port 812 is disposed closer to the distal end of the elongate shaft 804 to minimize the required length of the guidewire (not shown) for use therewith.

Catheter assembly 800 also includes a channel 814 providing access to the guidewire lumen 820 from the exterior of the catheter shaft 804. The channel 814, which may be shaped as described with reference to FIGS. 1D and 1E, extends from the proximal guidewire port 812 to a proximal channel end 816. The channel 814 may have any suitable length and may even be omitted while maintaining single operator exchange capabilities.

With reference to FIG. 17, the proximal shaft portion 806 includes a guidewire lumen 820 and an ancillary lumen 822. Although a single ancillary lumen 822 is illustrated, any number of ancillary lumens may be utilized to suit the particular clinical application. With reference to FIG. 18, the distal shaft portion 808 includes a common guidewire and ancillary lumen 824. The common lumen 824 accommodates the guidewire (not shown) extending through the distal portion 808 of the elongate shaft 804 and also accommodates the passage of fluid from the ancillary lumen 822 of the proximal shaft portion 806. Accordingly, the common lumen 824 is in communication with both the guidewire lumen 820 and the ancillary lumen 822.

By providing a common lumen 824 to accommodate the guidewire and the passage of fluid from the ancillary lumen 822, the distal shaft portion 808 may have a reduced profile for accessing tortuous and/or small diameter duct pathways. Specifically, because separate guidewire and ancillary lumens are eliminated in favor of common lumen 824, a separation layer is not necessary. Eliminating the need for a separation layer proportionately reduces the profile of the distal shaft portion 808.

In order to eliminate the egress of fluid from the common lumen 824 out the proximal guidewire port 812, it is preferable to provide a seal 830 adjacent the proximal guidewire port 812. Preferably, the seal 830 provides a fluid seal with or without the guidewire disposed therein. The seal 830 may be located at the junction between the distal end of the proximal shaft portion 806 and the proximal end of the distal shaft portion 808.

Alternatively, the seal 830 may be located distal of the proximal guidewire port 812 such that a short length of the guidewire is constrained in the guidewire lumen proximal of the seal 830. Constraining the guidewire proximal of the seal 830 may be beneficial if a floppy guidewire is used and/or the guidewire encounters friction at the seal 830. Constraining the guidewire reduces the potential for the guidewire to buckle as it is being inserted into the seal 830. The guidewire may also be constrained by providing a separate tube extending a short distance proximally from the proximal guidewire port 812.

Generally, the seal 830 may be an active-type seal or a passive-type seal. An active-type seal requires activation by the user such as by pressure or the transmission of force. For example, an active-type seal may comprise an inflatable balloon which, upon inflation, seals the proximal guidewire exit port. A passive-type seal, by contrast, does not necessarily require activation by the user.

Passive-type seals include, but are not limited to, gap-type seals and interference-type seals. Gap-type seals provide a gap that is sized sufficiently small to inhibit the egress of fluid. For sealing about a guidewire, gap-type seals are sized to provide a gap between the seal and the guidewire, wherein the gap is sized sufficiently small to inhibit the egress of fluid, but is sufficiently large to allow the guidewire to freely move. For example, a gap-type seal may be provided by a tube having an inside diameter slightly larger than the outside diameter of the guidewire.

Interference-type seals, by contrast, provide contact between surfaces to inhibit the egress of fluid. For example, for sealing about a guidewire, an interference-type seal may be provided by an elastic tube having an inside diameter slightly smaller than the outside diameter of the guidewire, wherein the elastic tube dilates in response to the guidewire passing therethrough. The inside diameter of the elastic tube preferably includes a lubricious surface or coating to allow the guidewire to move freely.

An additional example of an interference-type seal comprises a flattened polymer tube or opposing polymer flaps in the shape of a duckbill. The duckbill-type seal may form a seal with or without a guidewire disposed therein. If used to seal about a guidewire, the flaps readily deflect to allow free movement of the guidewire.

As compared to other types of seals, a duckbill-type seal has the advantage of providing an effective fluid seal with or without the guidewire disposed therein. In addition, a duckbill-type valve provides a one-way valve, wherein fluid may move in one direction (e.g., a distal direction), but is prohibited from moving in the other direction (e.g., a proximal direction toward the guidewire port 812). Although virtually any type of seal may be utilized, for purposes of clarity and illustration, a duckbill-type one-way valve 830 capable of sealing about a guidewire is discussed herein.

Refer now to FIG. 19A, which illustrates a detailed side view of a first embodiment of the junction between the proximal shaft portion 806 and the distal shaft portion 808. FIGS. 20A–22A are cross-sectional views taken along lines 20A—20A, 21A—21A and 22A—22A, respectively, in FIG. 19A. As best seen in 20A, a seal 830 is disposed adjacent the proximal guidewire port 812. The seal 830, in this exemplary embodiment, is a duckbill-type one-way valve. However, the seal 830 may comprise any of the types discussed previously.

Duckbill-type valve 830 may comprise an elastomeric tube 831 mounted to a rigid tube 832 disposed in the guidewire lumen at the juncture between the proximal shaft portion 806 and the distal shaft portion 808. The elastic tube 831 may have a flattened distal portion or may comprise a tubular structure having opposing flaps formed in the distal end thereof by cutting two opposing slits through the wall of the tubular structure. Rigid tube 832 may comprise a stainless steel hypotube or other similar material having an inside diameter suitable to accommodate a guidewire therein. Elastic tube 831 may comprise an elastomer or any suitable elastic material. Both the elastic tube 831 and the rigid tube 832 may have a lubricious coating therein to reduce guidewire friction. Preferably, the duckbill-type valve 830 forms a fluid-type seal regardless of whether the guidewire is disposed therein. For purposes of illustration, seal 830 is shown with the flaps of the elastic tube 831 in the open position as they would appear with a guidewire (not shown) disposed therein. Without the guidewire disposed therein, of course, the flaps would be closed to form a fluid tight seal.

The distal end of the proximal shaft portion 806 may be necked down and inserted into an expanded proximal end of the distal shaft portion 808. The ends of the proximal shaft portion 806 and the distal shaft portion 808 may be secured by utilizing a suitable adhesive or by thermal bonding. Alternatively, the proximal end of the distal shaft portion 808 may be connected to the distal end of the proximal shaft portion 806 by utilizing a metal ring that is swaged or crimped onto the expanded proximal end of the distal shaft portion 808. If the proximal shaft portion 806 and the distal shaft portion 808 are bonded using thermal means, a tie layer may be utilized to the extent that the shaft portions comprise different materials having different adhesion characteristics.

Refer now to FIG. 19B, which illustrates a detailed side view of a second embodiment of the junction between the proximal shaft portion 806 and the distal shaft portion 808. Except as described herein, the embodiment illustrated in 19B is the same in form and function as the embodiment illustrated in FIG. 19A. FIGS. 20B–22B are cross-sectional views taken along lines 20B—20B, 21B—21B and 22B—22B, respectively, in FIG. 19B.

As best seen in FIG. 20B, a hood 840 is provided adjacent the proximal guidewire port 812 to facilitate easy insertion of the guidewire. Hood 840 includes an enlarged proximal portion 842, preferably having an oval shape, wherein the minor diameter is approximately equal to the diameter of the proximal shaft portion 806 and the major diameter is substantially larger than the proximal shaft portion 806. The proximal portion 842 defines an entrance 846 that has a diameter substantially larger than the diameter of the proximal guidewire port 812, and into which the guidewire may be easily inserted. The proximal end of the distal shaft portion 808 may include a flared portion 844 to provide a smooth transition from the hood 840.

Refer now to 19C, which illustrates a detailed side view of a third embodiment of the junction between the proximal shaft portion 806 and the distal shaft portion 808. Except as described herein, the embodiment illustrated in FIG. 19C is the same in form and function as the embodiment illustrated in FIG. 19A. In addition, although not illustrated, the hood 840 discussed with reference to FIG. 19B may be utilized in the embodiment illustrated in FIG. 19C. FIGS. 20C–22C are cross-sectional views taken along lines 20C—20C, 21C—21C and 22C—22C, respectively, in FIG. 19C.

As best illustrated in FIG. 20C, this embodiment differs from the embodiments described previously in that the distal shaft portion 808 is inserted into a cored-out portion of the proximal shaft portion 806. Specifically, the distal end of the proximal shaft portion 806 is cored or hollowed to define a circular interior with a single wall exterior. The proximal end of the distal shaft portion 808 is inserted into the cored distal end of the proximal shaft portion 806 and secured thereto by suitable means such as adhesive or thermal bonding.

To facilitate a smooth transition from the proximal shaft portion 806 to the distal shaft portion 808, a hood 850 is provided at the proximal end of the distal shaft portion 808. Hood 850 includes a flared proximal portion 852 and a distal portion 854 inserted into the common lumen 824 of the distal shaft portion 808. The flared portion 852 of the hood 850 facilitates the smooth insertion of the guidewire from the seal 830 into the common lumen 824.

Figure 23A:
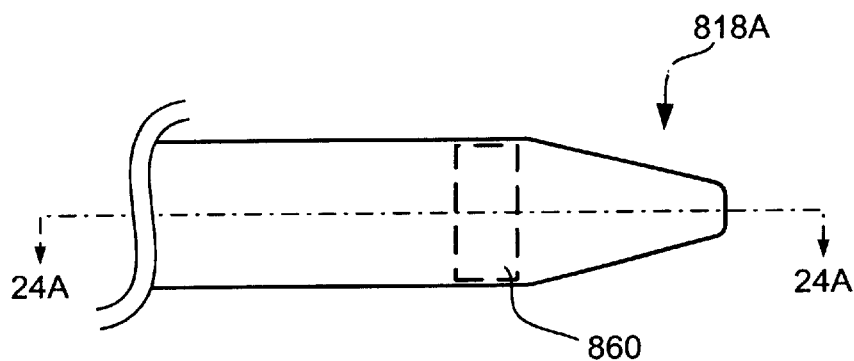
FIGS. 23A–23C are detailed side views of several embodiments of section 23 in FIG. 16.
Figure 23B:
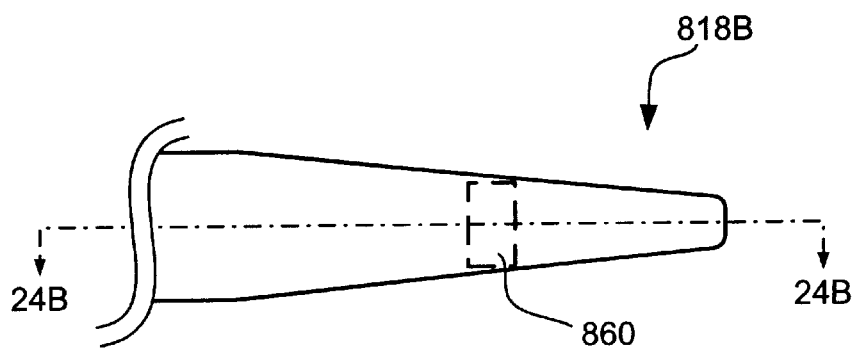
Figure 23C:
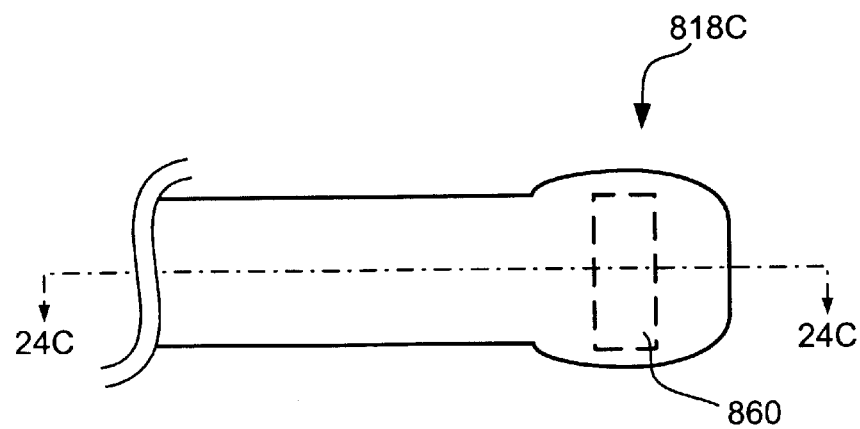
Figure 24A:
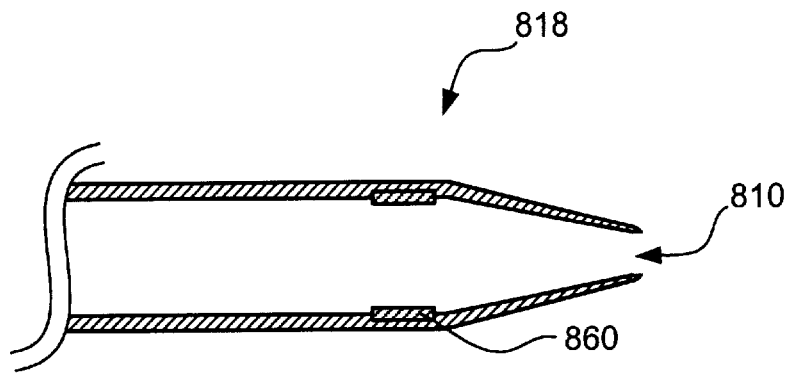
FIGS. 24A–24C are cross-sectional views taken along lines 24A—24A, 24B—24B, and 24C—24C in FIGS. 23A–23C, respectively.
Figure 24B:
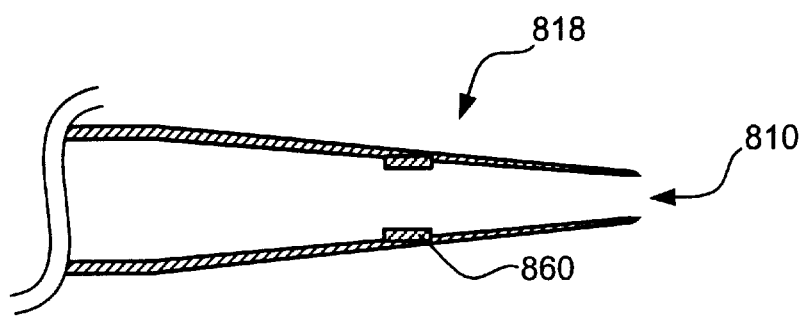
Figure 24C:
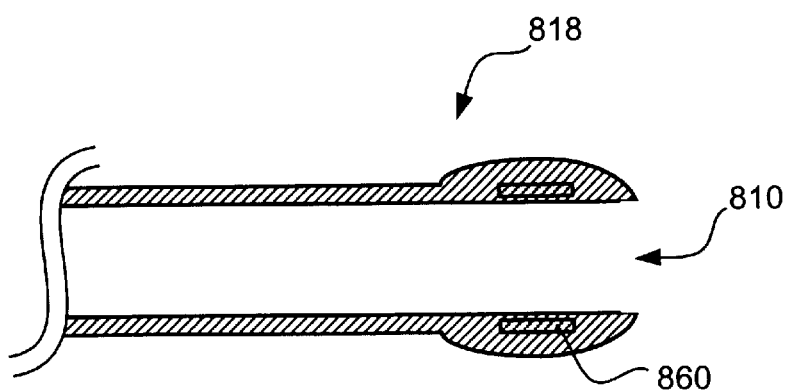

Refer now to FIGS. 23A–23C, which illustrate side views of several embodiments of the distal tip 818 of the distal shaft portion 808. FIGS. 24A–24C illustrate cross-sectional views taken along lines 24A—24A, 24B—24B and 24C—24C in FIGS. 23A–23C, respectively. The distal tip 818 may have a blunt-tapered tip 818A as illustrated in FIG. 23A, a gradually-tapered tip 818B as illustrated in FIG. 23B or a ball-shaped tip 818C as illustrated in FIG. 23C. Although illustrated as having a linear shape, the distal shaft portion 808 and the distal tip 818 may have a curve or other contour to facilitate navigation and steering of the distal end of the catheter 800. The desired shape of the tip 818 may be selected based on the particular clinical application and the particular duct pathway being navigated. The tip shapes illustrated in FIGS. 23A–23C are merely exemplary as many different shapes and sizes may be employed.

In each of the embodiments, a radiopaque marker band 860 may be disposed in the distal tip 818, preferably inside the tip 818 so as to not affect the profile or shape of the tip 818. The radiopaque marker band 860 facilitates fluoroscopic visualization of the distal end of the catheter 800. Although not illustrated, the distal shaft portion 808 and the distal tip 818 may also include a series of stripes having predetermined length, color, and position to facilitate exact longitudinal positioning of the catheter 800 relative to the endoscope (not shown).

In use, the catheter 800 may be used in substantially the same way as catheter 30 described previously. The primary difference, of course, is that catheter 800 utilizes a common distal lumen for the guidewire and the delivery of fluids from the ancillary lumen. Although the use of a common distal lumen may require the use of a seal at the proximal guidewire port as described herein, the catheter 800 operates and performs substantially the same as catheter 30. The primary difference in performance relates to the distal shaft portion 808. Specifically, the distal shaft portion 808 has a lower profile. Further, the single lumen design allows the distal shaft portion 808 and the distal tip 818 to be formed in a wide variety of shapes, curves, and sizes.

Refer now to FIG. 25, which illustrates a plan view of a single operator exchange catheter assembly 900 in accordance with another embodiment of the present invention. Catheter assembly 900 includes a standard hub assembly 902 connected to the proximal end of an elongate shaft 904. Elongate shaft 904 includes a proximal portion 906 and a distal portion 908. Proximal shaft portion 906 includes a plurality of walls 924 defining a guidewire lumen 920 (not shown) and at least one ancillary lumen 922 (not shown).

Distal shaft portion 908 includes a wall 926 defining a distal lumen 928. Distal lumen 928 terminates at its distal end with a distal guidewire port 910.

Catheter assembly 900 also includes a channel 914 defined by wall 924 of proximal shaft portion 906. Channel 914 includes a proximal end 916 and a distal end 918. In the embodiment of FIG. 25, channel 914 provides access to guidewire lumen 920 from the exterior of proximal shaft portion 906. Walls 924 of proximal shaft portion 906 define a proximal guidewire port 912 (not shown). A guidewire may enter guidewire lumen 920 of proximal shaft portion 906 by passing through guidewire port 912.

A flare 930 is also disposed proximate distal end 918 of channel 914. A removable hood assembly 940 is disposed about proximal shaft 906 proximate channel 914. Flare 930 and removable hood assembly 940 may each aid in directing a guidewire toward proximal guidewire port 912. The portion of catheter assembly 900 in which flare 930 and removable hood assembly 940 are disposed may be generally referred to as an entry region 950. Various embodiments of entry region 950 of catheter assembly 900 are discussed in more detail below.

Refer now to FIG. 26, which is a detailed plan view of entry region 950 of one embodiment of catheter assembly 900. In the embodiment of FIG. 26, flare 930 includes an enlarged portion 932 formed from a portion of wall 924 of proximal shaft portion 906. One method which may be utilized to form flare 930 is to apply heat to wall 924 proximate distal end 918 of channel 914. When wall 924 has reached a desired temperature, flare 930 may be formed using a mandrel, pliers, or other tools. Enlarged portion 932 of flare 930 defines a flare entry port 934 adapted to guide a guidewire toward proximal guidewire port 912 (not shown).

In FIG. 26, removable hood assembly 940 is disposed about proximal shaft portion 906, proximally of flare 930. Removable hood assembly 940 is comprised of a generally tubular body portion 946, an enlarged portion 942, a tab portion 948, and a preferential tear line 952. Enlarged portion 942 of removable hood assembly 940 defines a hood entry port 944.

In the embodiment of FIG. 26, preferential tear line 952 is comprised of a plurality of perforations 954. Other embodiments of perforations 954 are possible without deviating from the spirit and scope of the present invention. For example, perforations 954 may comprise holes, slots, slits, or dimples. Likewise, other embodiments of preferential tear line 952 are possible without deviating from the spirit and scope of the present invention. For example, preferential tear line 952 may comprise a groove, or a fold.

Embodiments of the present invention have been envisioned in which removable hood assembly 940 does not include preferential tear line 952, and embodiments have been envisioned in which removable hood assembly 940 includes a plurality of preferential tear lines 952. In one method in accordance with the present invention, removable hood assembly 940 is removed from proximal shaft portion 906 by grasping tab portion 948 and applying a pulling force which causes body portion 946 of removable hood assembly 940 to tear along preferential tear line 952. In this manner, removable hood assembly 940 may be selectively removed from proximal shaft portion 906.

FIG. 27 is a partial perspective view of a preferred detachable hood design for the catheter 900 of FIG. 25 and entry region 950 of FIG. 26. A guidewire 901 is shown inserted into entrance 951 of hood 940. In use, the guidewire 901 will extend into the guidewire lumen 920 of FIG. 28 through the proximal guidewire port 912, also shown in FIG. 28. FIG. 27 particularly illustrates how the preferred shape of hood 940 aids in guidewire insertion into the common guidewire and ancillary lumen 928. Hood entrance 951 gradually reduces in diameter from enlarged proximal portion 905 into the opening of proximal guidewire port 912. As the guidewire 901 is inserted into the hood, the gradually reducing diameter forces the guidewire 901 into the opening of the proximal guidewire port 912. The guidewire 901 may then be further fed through the valve or seal 960 disposed distal of the proximal guidewire port 912, entering the common guidewire and ancillary lumen 928. As also depicted in FIG. 27, the proximalmost shape 905 of the hood generally matches the lumen 903 within which the hood is disposed. This prevents a guidewire from passing by the hood when inserted into lumen 903.

Figure 28:
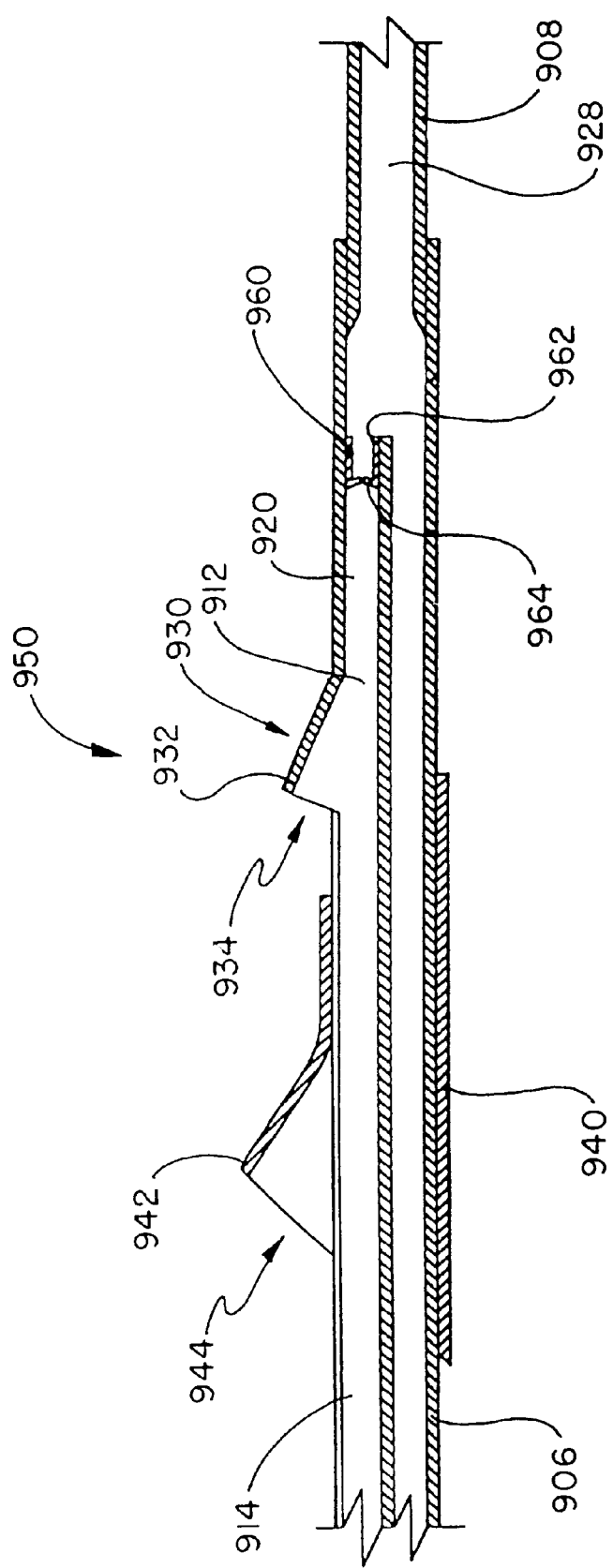
FIG. 28 is a detailed cross-sectional view of an entry region of one embodiment of the single operator exchange catheter of FIG. 25.

Refer now to FIG. 28 which is a cross-sectional view of entry region 950 of catheter assembly 900. In FIG. 28, it may be appreciated that hood entry port 944 of removable hood assembly 940 is in fluid communication with channel 914 of proximal shaft portion 906. When the end of a guidewire is inserted into hood entry port 944, removable hood assembly 940 guides the guidewire into channel 914 of proximal shaft portion 906. If the guidewire is urged further in a distal direction it will enter guidewire lumen 920 via proximal guidewire port 912. If the guidewire is urged still further in a distal direction, it will pass through a valve 960 which is disposed within guidewire lumen 920. If the guidewire is urged still further in a distal direction, it will enter distal lumen 928 of distal shaft portion 908.

Valve 960 is comprised of a body portion 962, and a plurality of sealing portions 964. Body portion 962 and sealing portions 964 may be comprised of the same materials or different materials. In a presently preferred embodiment, body portion 962 and sealing portions 964 are both comprised of thermoplastic elastomer (TPE).

Figure 29:
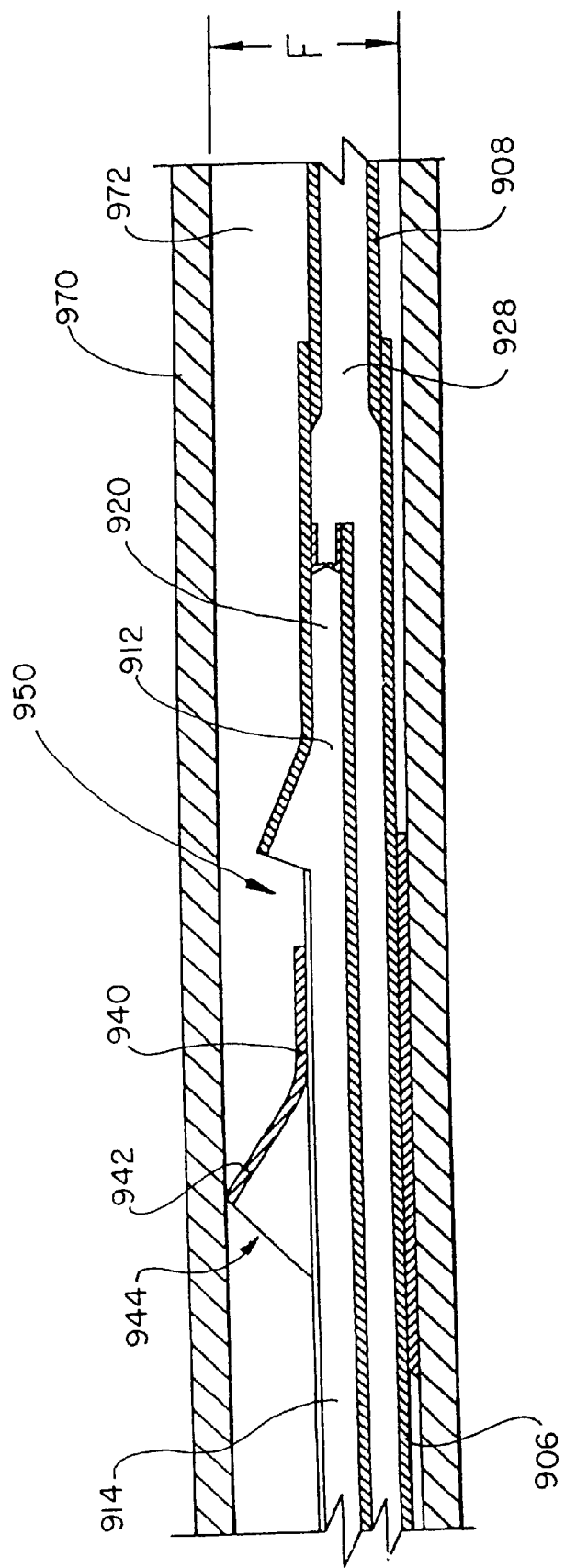
FIG. 29 is a detailed cross-sectional view of an entry region of one embodiment of the single operator exchange catheter of FIG. 25 disposed within a lumen of a device.

Refer now to FIG. 29 which is a cross-sectional view of entry region 950 of catheter assembly 900. In FIG. 29, catheter assembly 900 has been positioned within a lumen 972 defined by a device 970. Device 970 may be any device intended for use with catheter assembly 900. For example, device 970 may be an endoscope, a sheath, a guide catheter, or an introducer. As shown in FIG. 29, lumen 972 of device 970 has a diameter of F. In a presently preferred embodiment, the outer diameter of removable hood assembly 940 is substantially equal to lumen diameter F.

A guidewire may be inserted into lumen 972 of device 972 and urged in a distal direction until it encounters removable hood assembly 940. As shown in FIG. 29, removable hood assembly 940 is adapted to guide the end a guidewire into channel 914. In a presently preferred embodiment, removable hood assembly 940 extends substantially across lumen 972 of device 970. In this manner, removable hood assembly 940 is adapted to prevent the guidewire from bypassing hood entry port 944.

Figure 30:
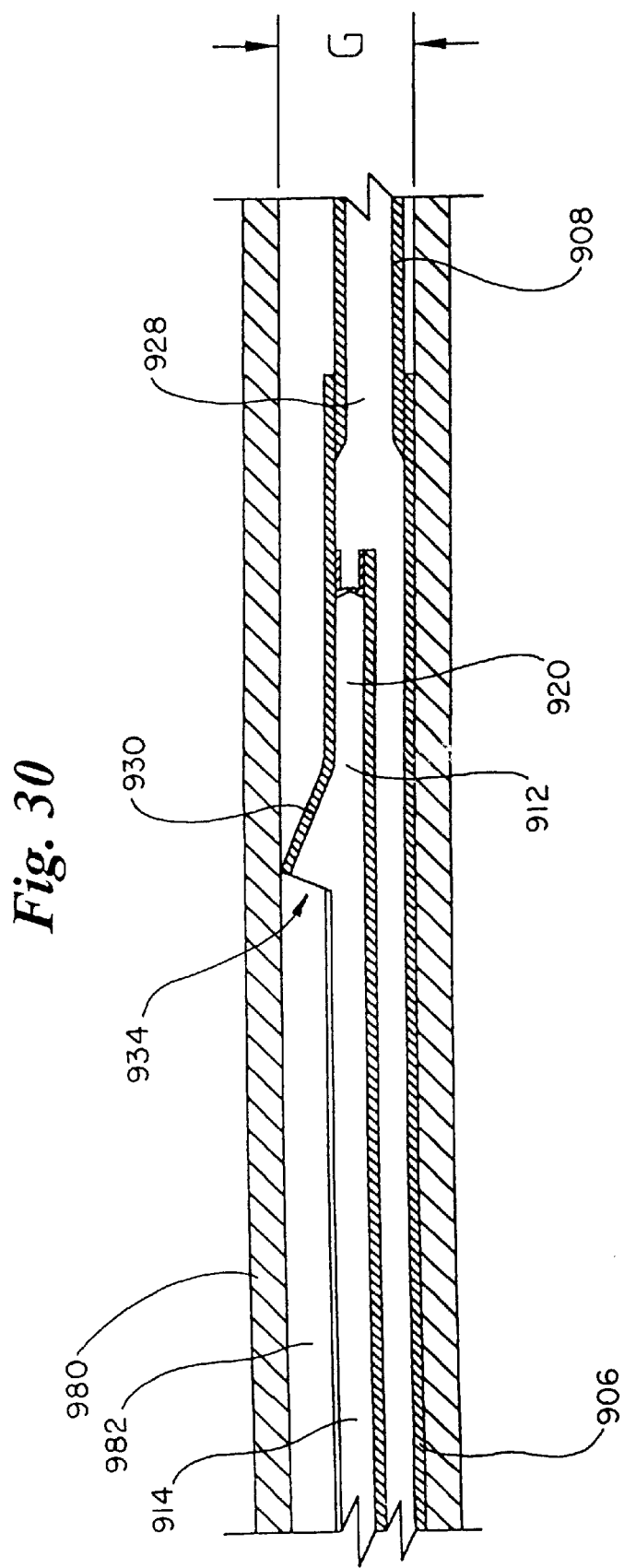
FIG. 30 is a detailed cross-sectional view of an entry region of one embodiment of the single operator exchange catheter of FIG. 25 disposed within a lumen of a device.

Refer now to FIG. 30 which is a cross-sectional view of entry region 950 of catheter assembly 900. In FIG. 30, removable hood assembly has been removed from proximal shaft portion 906 and catheter assembly 900 has been positioned within a lumen 982 defined by a device 980. As in the previous FIG., device 980 may be any device intended for use with catheter assembly 900. For example, device 980 may be an endoscope, a sheath, a guide catheter, or an introducer. As shown in FIG. 30, lumen 982 of device 980 has a diameter of G. In a presently preferred embodiment, the outer diameter of catheter assembly 900 proximate flare 930 is substantially equal to lumen diameter G.

A guidewire may be inserted into lumen 982 of device 980 and urged distally until it reaches flare 930. When the distal end of a guidewire encounters flare 930, it will pass through flare entry port 934. As shown in FIG. 30, flare 930 is adapted to guide the end a guidewire into proximal guidewire port 912. In a presently preferred embodiment, the portion of catheter assembly 900 proximate flare 930 extends substantially across lumen 982 of device 980. In this manner, flare 930 is adapted to prevent the guidewire from bypassing flare entry port 934.

By referring to FIGS. 29 and 30 simultaneously, it may be appreciated that a physician may purchase a single catheter assembly 900, and use that catheter assembly in conjunction with both device 970 and device 980. In fact, a single catheter assembly may be used with a plurality of devices. When removable hood assembly 940 is disposed about proximal shaft portion 906 of catheter assembly 900, catheter assembly 900 may be used in conjunction with any device having a lumen with a diameter similar to diameter F. Removable hood assembly 940 may be selectively removed to adapt catheter assembly 900 for use with any device having a lumen with a diameter similar to diameter G. It should be noted that in a presently preferred embodiment, both removable hood assembly 940 and flare 930 are substantially flexible, so that they may be inserted into lumens having various diameters. Embodiments of catheter assembly 900 have also been envisioned which include more than one removable hood assembly 940.

The distal end of proximal shaft portion 906 is disposed within expanded proximal end 956 of distal shaft portion 908. A ring 966 is disposed about expanded proximal end 956 of distal shaft portion 908. In a presently preferred embodiment, ring 966 is swaged or crimped to fix expanded proximal end 956 of distal shaft portion 908 to distal end 958 of proximal shaft portion 906. Distal end 958 of proximal shaft portion 906 may also be fixed to expanded proximal end 956 of distal shaft portion 908 utilizing a suitable adhesive or by thermal bonding.

As described above, when the end of a guidewire is inserted into either flare entry port 934 or hood entry port 944, the guidewire will be directed into channel 914 of proximal shaft portion 906. If the guidewire is urged further in a distal direction it will enter guidewire lumen 920 via proximal guidewire port 912. If the guidewire is urged still further in a distal direction, it will pass through a valve 960 which is disposed within guidewire lumen 920. If the guidewire is urged still further in a distal direction, it will enter distal lumen 928 of distal shaft portion 908.

As best illustrated in FIG. 28, distal lumen 926 of distal shaft portion 908 is in fluid communication with guidewire lumen 920 of proximal shaft portion 908. In the embodiment of FIGS. 26–30, the proximal end of distal shaft portion 908 is disposed within the distal portion of the proximal shaft portion 906. The distal end of the proximal shaft portion 906 is cored or hollowed to define a circular interior with a single wall exterior. The proximal end of the distal shaft portion 908 has been inserted into this cored portion of proximal shaft portion 906 and secured thereto by suitable means such as adhesive or thermal bonding. Those of skill in the art will appreciate that other embodiments of entry region 950 are possible without deviating from the spirit and scope of the present invention. An additional exemplary embodiment is illustrated in FIG. 31.

Figure 31:
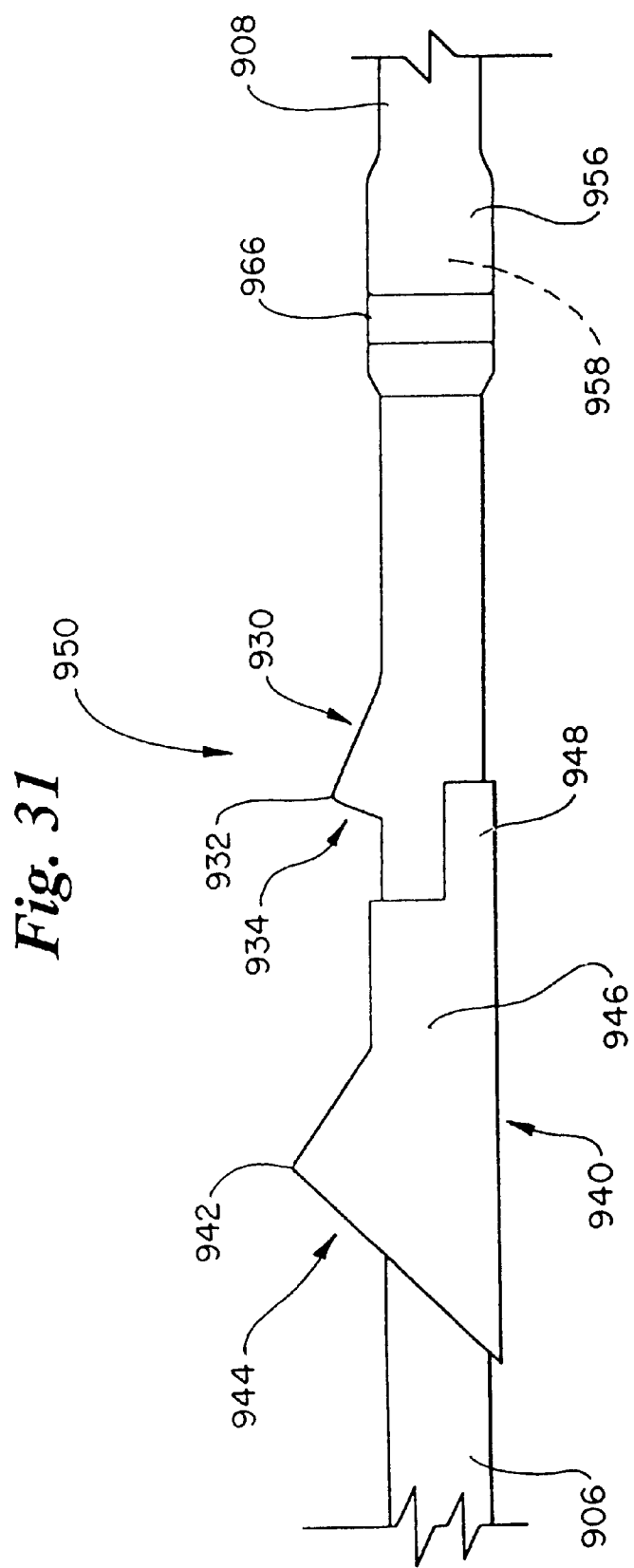
FIG. 31 is a detailed plan view of an entry region of one embodiment of the single operator exchange catheter of FIG. 25.

Refer now to FIG. 31, which is a detailed plan view of an additional embodiment of entry region 950 of catheter assembly 900. In the embodiment of FIG. 31, distal shaft portion 908 includes an expanded proximal end 956. A distal end 958 of proximal shaft portion 906 is disposed within expanded proximal end 956 of distal shaft portion 908. A ring 966 is disposed about expanded proximal end 956 of distal shaft portion 908. In a presently preferred embodiment, ring 966 is swaged or crimped to fix expanded proximal end 956 of distal shaft portion 908 to distal end 958 of proximal shaft portion 906. Distal end 958 of proximal shaft portion 906 may also be fixed to expanded proximal end 956 of distal shaft portion 908 utilizing a suitable adhesive or by thermal bonding.

A flare 930 is disposed on proximal shaft 906. Flare 930 includes an enlarged portion 932 formed from a portion of wall 924 of proximal shaft portion 906. Enlarged portion 932 of flare 930 defines a flare entry port 934. A removable hood assembly 940 is disposed about proximal shaft portion 906, proximally of flare 930.

Removable hood assembly 940 is comprised of a generally tubular body portion 946, a enlarged portion 942, and a tab portion 948. Enlarged portion 948 of removable hood assembly 940 defines a hood entry port 944. In one method in accordance with the present invention, removable hood assembly 940 is removed from proximal shaft portion 906 by grasping tab portion 948 and applying a pulling force which causes body portion 946 of removable hood assembly 940 to tear. In this manner, removable hood assembly 940 may be selectively removed from proximal shaft portion 906.

Figure 32:
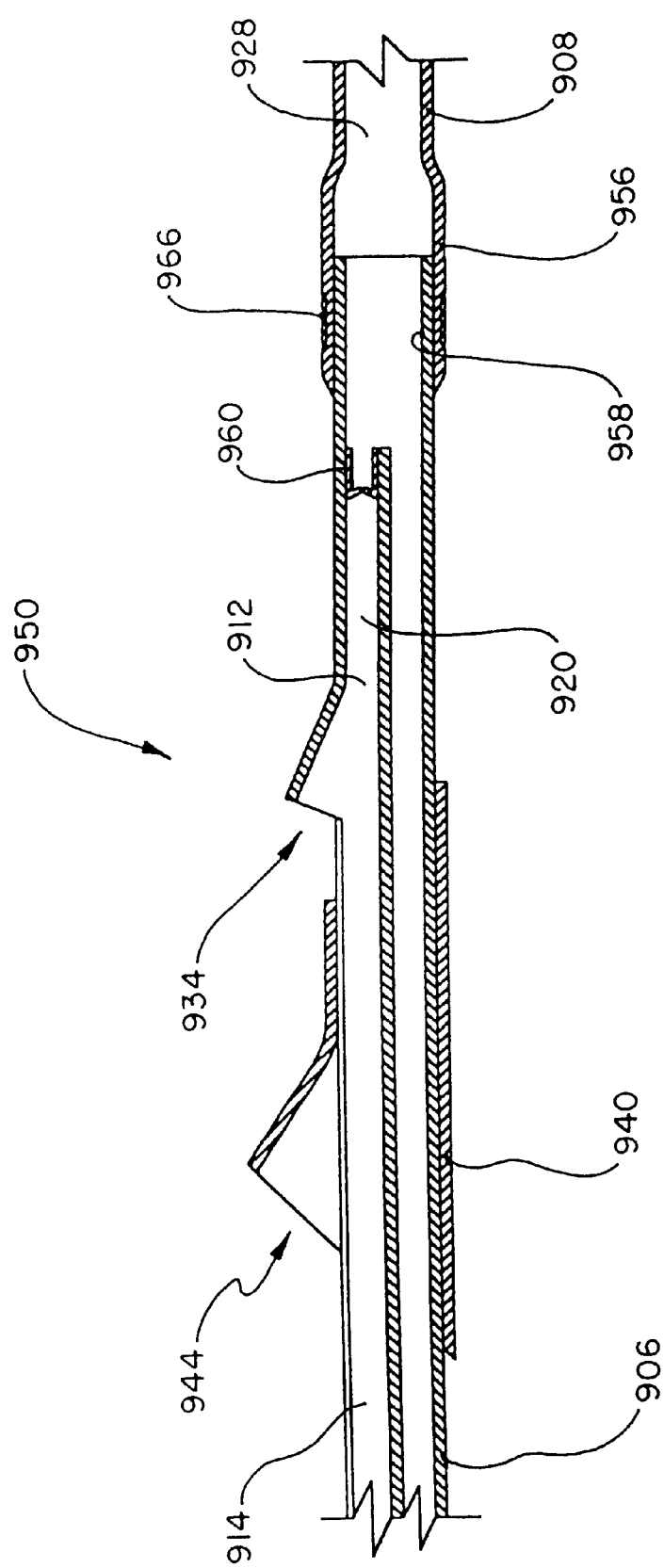
FIG. 32 is a detailed cross-sectional view of an entry region of one embodiment of the single operator exchange catheter of FIG. 25.

Refer now to FIG. 32 which is a cross-sectional view of entry region 950 of catheter assembly 900. In FIG. 32, it may be appreciated that both flare entry port 934 and hood entry port 944 are in fluid communication with channel 914 of proximal shaft portion 906. When the end of a guidewire is inserted into either flare entry port 934 or hood entry port 944, the guidewire will be directed into channel 914 of proximal shaft portion 906. If the guidewire is urged further in a distal direction it will enter guidewire lumen 920 via proximal guidewire port 912. If the guidewire is urged still further in a distal direction, it will pass through a valve 960 which is disposed within guidewire lumen 920. If the guidewire is urged still further in a distal direction, it will enter distal lumen 928 of distal shaft portion 908.

Those skilled in the art will recognize that the present invention may be manifested in a wide variety of forms other than the specific embodiments contemplated and described herein. Accordingly, departures in form and detail may be made without departing from the scope and spirit of the present invention as described in the appended claims.

What is claimed is:

1. A biliary catheter for use in combination with a guidewire and an endoscope, comprising:

an elongate shaft having a proximal end, a distal end and a lumen extending therethrough;

a distal guidewire port defined by the elongate shaft and disposed at the distal end thereof, the port being in fluid communication with the lumen of the elongate shaft;

a slot defined by a wall of the elongated shaft and disposed between the proximal end of the elongate shaft and the distal guidewire port, the slot being in fluid communication with the lumen of the elongate shaft; and a hood member disposed about the elongate shaft proximate the slot;

wherein the hood member has a proximal end and a distal end and an internal passage therebetween, the internal passage having a diameter that decreases from the proximal end to the distal end.

2. A biliary catheter as in claim 1, wherein the hood member defines a hood entry port.

3. A biliary catheter as in claim 1, wherein the hood member defines a hood entry port, the hood entry port being in fluid communication with the slot.

4. A biliary catheter as in claim 1, wherein the hood member comprises a generally tubular body.

5. A biliary catheter as in claim 1, wherein the hood member includes a generally tubular body, and a tab.

6. A biliary catheter as in claim 1, further comprising a flare disposed proximate a distal end of the slot, the flare defining a flare entry port in fluid communication with the slot.

7. A biliary catheter as in claim 1, further comprising a seal disposed within the lumen of the elongate shaft distally of the slot.

8. A biliary catheter as in claim 7, wherein the seal provides a fluid seal about a guidewire disposed therein.

9. A biliary catheter as in claim 7, wherein the seal provides a fluid seal without a guidewire disposed therein.

10. A biliary catheter as in claim 7, wherein the seal is a one-way valve.

11. A biliary catheter as in claim 7, wherein the seal is an active-type seal.

12. A biliary catheter as in claim 7, wherein the seal is a passive-type seal.

13. A biliary catheter as in claim 7, wherein the seal is a gap-type seal.

14. A biliary catheter as in claim 7, wherein the seal is an interference-type seal.

15. A biliary catheter as in claim 7, wherein the seal comprises a plurality of flaps.

16. A biliary catheter as in claim 7, wherein the seal comprises a flattened tube.

17. A biliary catheter as in claim 1, wherein the elongate shaft includes a single lumen distal portion.

18. A biliary catheter as in claim 1, wherein the elongate shaft includes a bi-lumen proximal portion.

19. A biliary catheter as in claim 1, wherein the hood member is configured to fit within the endoscope.

20. A biliary catheter as in claim 19, wherein the hood member is configured to guide the guidewire through the slot into the lumen extending through the catheter while positioned within the endoscope.

21. A biliary catheter as in claim 1, wherein the hood member is configured to be removable from the elongate shaft.

22. A biliary catheter as in claim 1, wherein the hood member is flexible.

23. A method of using a biliary catheter, comprising the steps of:
   providing an endoscope;
   providing a guidewire;
   providing a biliary catheter wherein the catheter includes an elongate shaft having a proximal end, a distal end and a lumen extending therethrough, a slot defined by a wall of the elongated shaft and disposed between the proximal end of the elongate shaft and the distal end of the elongate shaft, the slot being in fluid communication with the lumen of the elongate shaft, and a hood member disposed about the elongate shaft proximate the slot, the hood member defining a hood entry port in fluid communication with the slot, the hood member having a proximal end and a distal end and an internal passage therebetween, the internal passage having a diameter that decreases from the proximal end to the distal end;
   inserting the endoscope into a patient;
   inserting the catheter into the endoscope;
   inserting the guidewire into the hood entry port;
   urging the guidewire distally into the slot; and
   urging the guidewire distally into the lumen of the elongate shaft.

24. A method of using a biliary catheter as in claim 20, wherein the catheter includes a seal disposed within the lumen of the elongate shaft, an the method includes the step of urging the guidewire through the seal.

25. A method of using a biliary catheter, comprising the steps of:
   providing an endoscope;
   providing a guidewire;
   providing a biliary catheter wherein the catheter includes an elongate shaft having a proximal end, a distal end and a lumen extending therethrough, a slot defined by a wall of the elongate shaft and disposed between the proximal end of the elongate shaft and the distal of the elongate shaft, the slot being in fluid communication with the lumen of the elongate shaft, a flare defining a flare entry point disposed proximate the distal end of the slot, and a hood member disposed about the elongate shaft proximate the slot;
   inserting the endoscope into a patient;
   removing the hood member from the catheter;
   inserting the catheter into the endoscope;
   inserting the guidewire into flare entry port;
   urging the guidewire distally into the slot; and
   urging the guidewire distally into the lumen of the elongate shaft.

26. A method of using a biliary catheter as in claim 25, wherein the catheter includes a seal disposed within the lumen of the elongate shaft, an the method includes the step of urging the guidewire through the seal.

27. A biliary catheter for use in combination with a guidewire and an endoscope, comprising:
   an elongate shaft having a proximal end, a distal end and a lumen extending therethrough;
   a distal guidewire port defined by the elongate shaft and disposed at the distal end thereof, the port being in fluid communication with the lumen of the elongate shaft;
   a slot defined by a wall of the elongated shaft and disposed between the proximal end of the elongate shaft and the distal guidewire port, the slot being in fluid communication with the lumen of the elongate shaft;
   a hood member disposed about the elongate shaft proximate the slot; and
   a flare disposed proximate a distal end of the slot.

* * * * *

UNITED STATES PATENT AND TRADEMARK OFFICE
CERTIFICATE OF CORRECTION

PATENT NO. : 6,520,951 B1
DATED : February 18, 2003
INVENTOR(S) : Oscar R. Carrillo, Jr. et al.

It is certified that error appears in the above-identified patent and that said Letters Patent is hereby corrected as shown below:

<u>Title page,</u>
Item [57], ABSTRACT
Line 12, delete "bitumen" and insert therefor -- bi-lumen --.

<u>Column 3,</u>
Line 17, delete "bitumen" and insert therefor -- bi-lumen --.

<u>Column 17,</u>
Line 13, delete "bitumen" and insert therefor -- bi-lumen --.

Signed and Sealed this

Twelfth Day of August, 2003

JAMES E. ROGAN
*Director of the United States Patent and Trademark Office*